United States Patent [19]
Jordan, III et al.

[11] Patent Number: 5,864,394
[45] Date of Patent: Jan. 26, 1999

[54] SURFACE INSPECTION SYSTEM

[75] Inventors: John R. Jordan, III, Mountain View; Mehrdad Nikoonahad, Atherton; Keith B. Wells, Santa Cruz, all of Calif.

[73] Assignee: Kla-Tencor Corporation, San Jose, Calif.

[21] Appl. No.: 536,862

[22] Filed: Sep. 29, 1995

Related U.S. Application Data

[63] Continuation-in-part of Ser. No. 263,203, Jun. 20, 1994, Pat. No. 5,576,831, and a continuation-in-part of Ser. No. 351,664, Dec. 8, 1994, abandoned, and a continuation-in-part of Ser. No. 499,995, Jul. 10, 1995, and a continuation-in-part of Ser. No. 361,131, Dec. 21, 1994, Pat. No. 5,530,550.

[51] Int. Cl.$^6$ ..................................................... G01N 21/00
[52] U.S. Cl. ........................... 356/237; 356/394; 356/398
[58] Field of Search .................................... 356/237, 394, 356/398

[56] References Cited

U.S. PATENT DOCUMENTS

| | | |
|---|---|---|
| 3,667,846 | 6/1972 | Nater et al. ............................... 356/120 |
| 3,851,951 | 12/1974 | Eveleth . |
| 4,391,524 | 7/1983 | Steigmeier et al. . |
| 4,405,238 | 9/1983 | Grobman et al. . |
| 4,441,124 | 4/1984 | Heebner et al. . |
| 4,532,650 | 7/1985 | Wihl et al. . |
| 4,556,290 | 12/1985 | Roulot . |
| 4,579,455 | 4/1986 | Levy et al. . |
| 4,589,773 | 5/1986 | Ido et al. . |
| 4,601,576 | 7/1986 | Galbraith . |
| 4,614,427 | 9/1986 | Koizumi et al. . |
| 4,650,983 | 3/1987 | Suwa . |
| 4,728,190 | 3/1988 | Knollenberg . |
| 4,748,333 | 5/1988 | Mizutani et al. . |
| 4,786,815 | 11/1988 | Walker et al. . |
| 4,805,123 | 2/1989 | Specht et al. . |
| 4,844,617 | 7/1989 | Kelderman et al. . |
| 4,864,123 | 9/1989 | Mizutani et al. . |

(List continued on next page.)

OTHER PUBLICATIONS

Clark et al., "Dynamic performance of a scanning X–Y stage for automated eletron–beam inspection", *J. Vac. Sci. Technol.*, B 10(6), Nov./Dec. 1992, pp. 2638–2642.

Alumont et al., "Dual sensor technology for high–speed detection of 0.1 micron defects", SPIE vol. 1926 Integrated Circuit Motrology, Inspection, and Process Control VII, 1993, pp. 1–12.

Warner et al., "Reviewing Angle–Resolved Methods for Improved Surface Particle Detection", *Microcontamination*, Sep./Oct. 1993, pp. 35–39 & 109.

Carmel et al., "New Directions in Process Control", SPIE vol. 2196, pp. 332–340.

Dralla et al., "Inspection of Patterned Wafers: 0.35 µm Design Rules and Beyond", presented at Semicon, Kansai, Japan, Jun. 15–17, 1994.

Gottlieb, "Acoustooptic Scanners and Modulators", publication of Westinghouse Electric Corporation, pp. 615–685.

*Primary Examiner*—Frank G. Font
*Assistant Examiner*—Reginald A. Ratliff
*Attorney, Agent, or Firm*—Majestic, Parsons, Siebert & Hsue

[57] ABSTRACT

A high throughput surface inspection system with enhanced detection sensitivity is described. The acquired data is processed in real time at a rate of below 50 MHz thereby reducing the cost for data processing. Anomalies are detected and verified by comparing adjacent repeating patterns and the height of the surface is monitored and corrected dynamically to reduce misregistration errors between adjacent repeating patterns. Local thresholds employing neighborhood information are used for detecting and verifying the presence of anomalies. The sampled point spread function of the combined illumination and collection system is exploited for anomaly detection and verification.

113 Claims, 14 Drawing Sheets

Microfiche Appendix Included
(3 Microfiche, 77 Pages)

U.S. PATENT DOCUMENTS

| | | |
|---|---|---|
| 4,864,147 | 9/1989 | Ikari et al. . |
| 4,889,998 | 12/1989 | Hayano et al. . |
| 4,891,526 | 1/1990 | Reeds . |
| 4,898,471 | 2/1990 | Stonestrom et al. . |
| 4,912,487 | 3/1990 | Porter et al. . |
| 4,926,489 | 5/1990 | Danielson et al. . |
| 4,936,676 | 6/1990 | Stauffer . |
| 4,966,455 | 10/1990 | Avni et al. . |
| 4,966,457 | 10/1990 | Hayano et al. . |
| 5,004,929 | 4/1991 | Kakinoki et al. . |
| 5,027,132 | 6/1991 | Manns et al. . |
| 5,030,008 | 7/1991 | Scott et al. . |
| 5,122,898 | 6/1992 | Picault . |
| 5,162,642 | 11/1992 | Akamatsu et al. . |
| 5,166,516 | 11/1992 | Kajimura . |
| 5,272,517 | 12/1993 | Tokura . |
| 5,298,976 | 3/1994 | Shahar et al. ............................ 356/375 |
| 5,317,380 | 5/1994 | Allemand . |
| 5,363,187 | 11/1994 | Hagiwara et al. . |
| 5,530,550 | 6/1996 | Nikoonahad et al. ................... 356/375 |
| 5,576,831 | 11/1996 | Nikoonahad et al. ................... 356/375 |

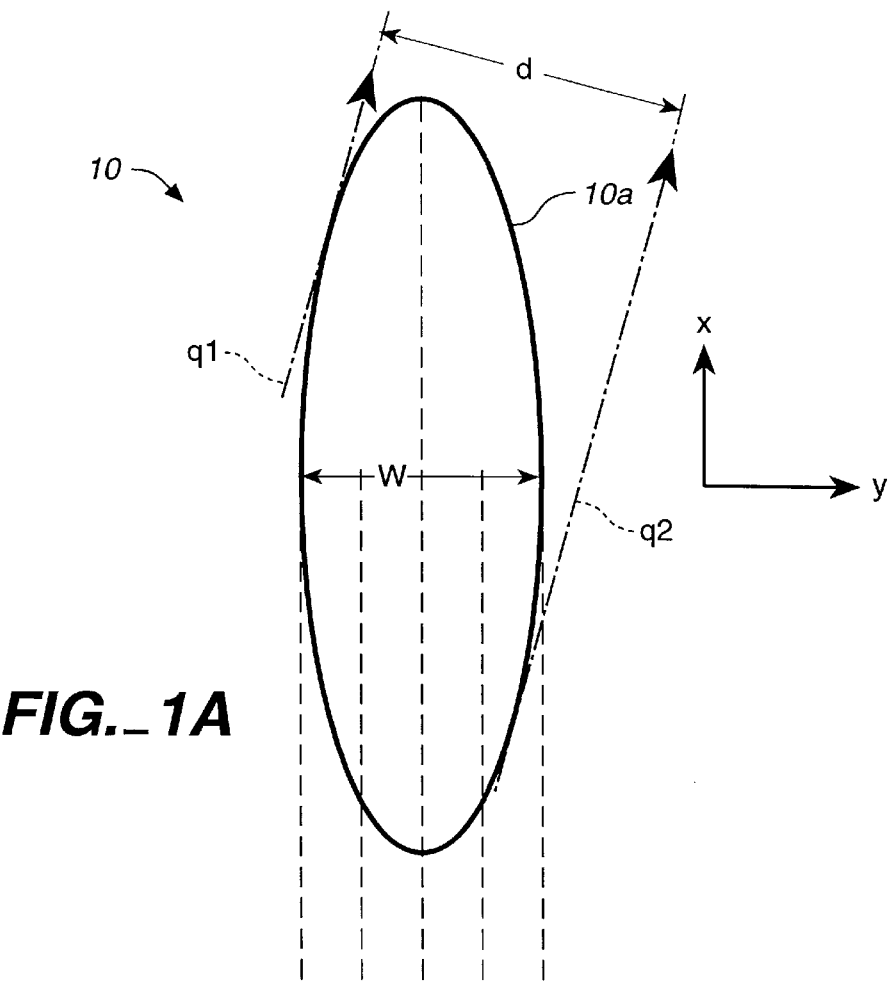
FIG._1A
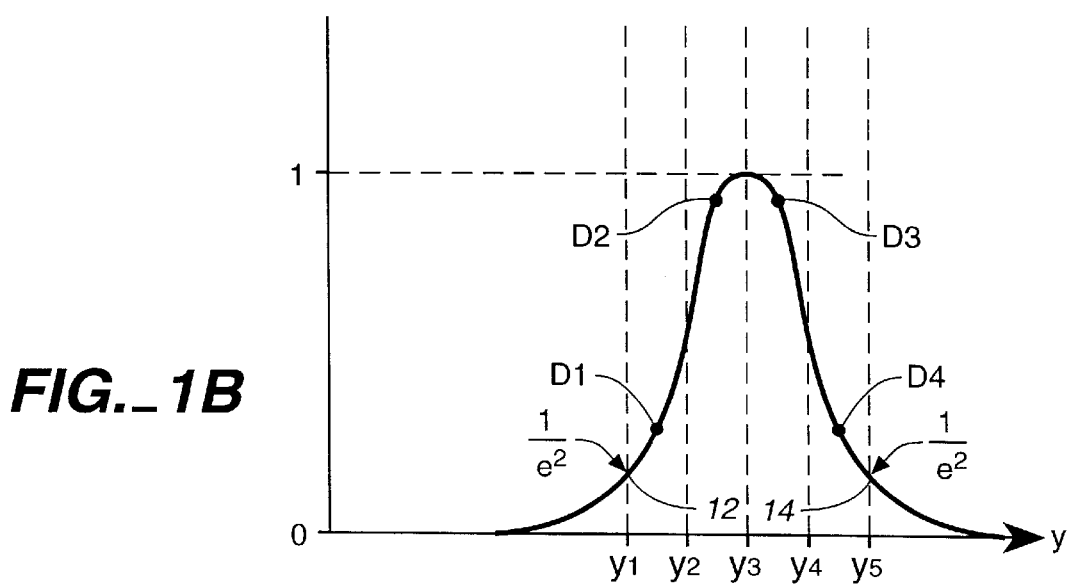
FIG._1B

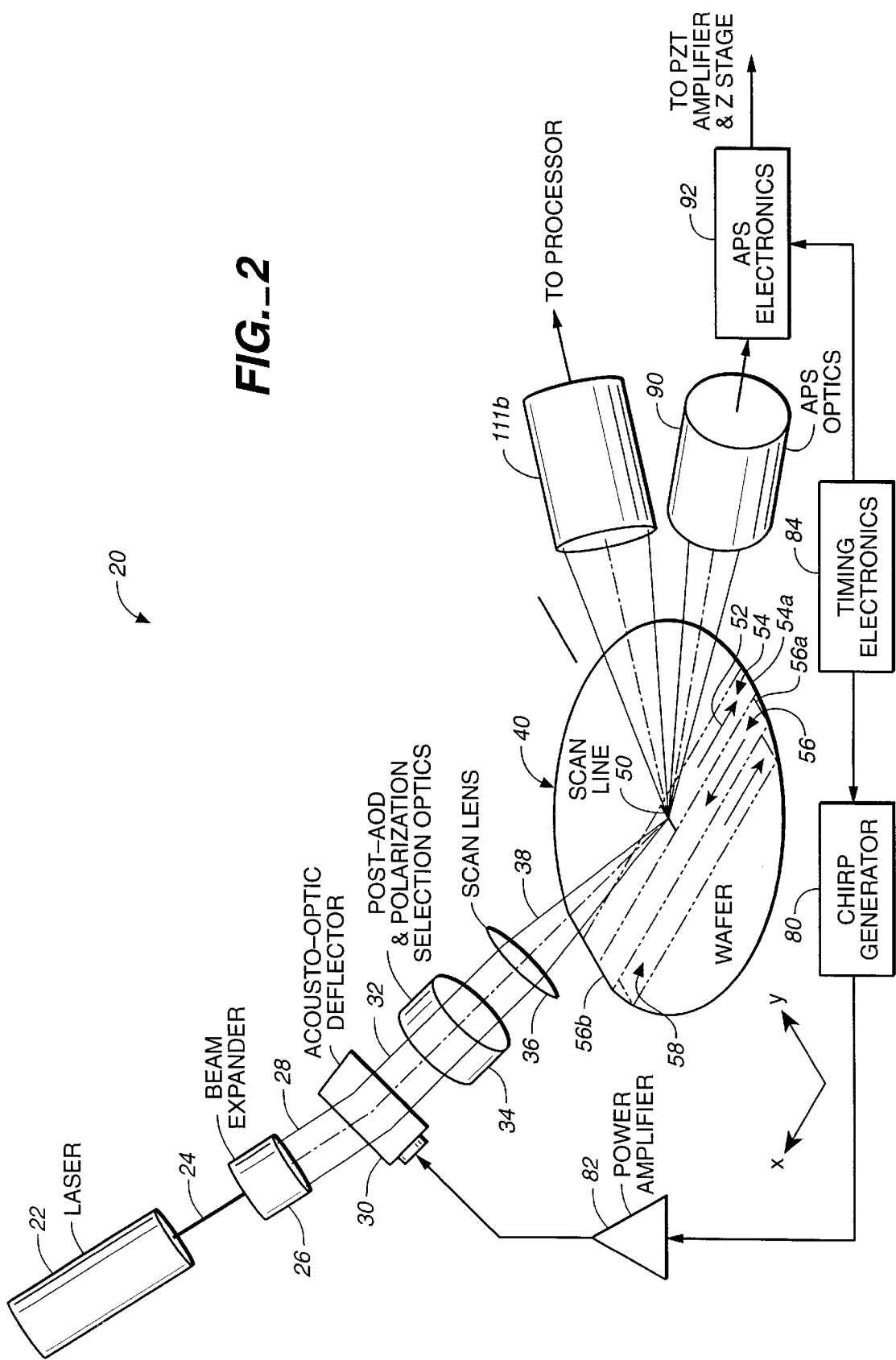
FIG._2

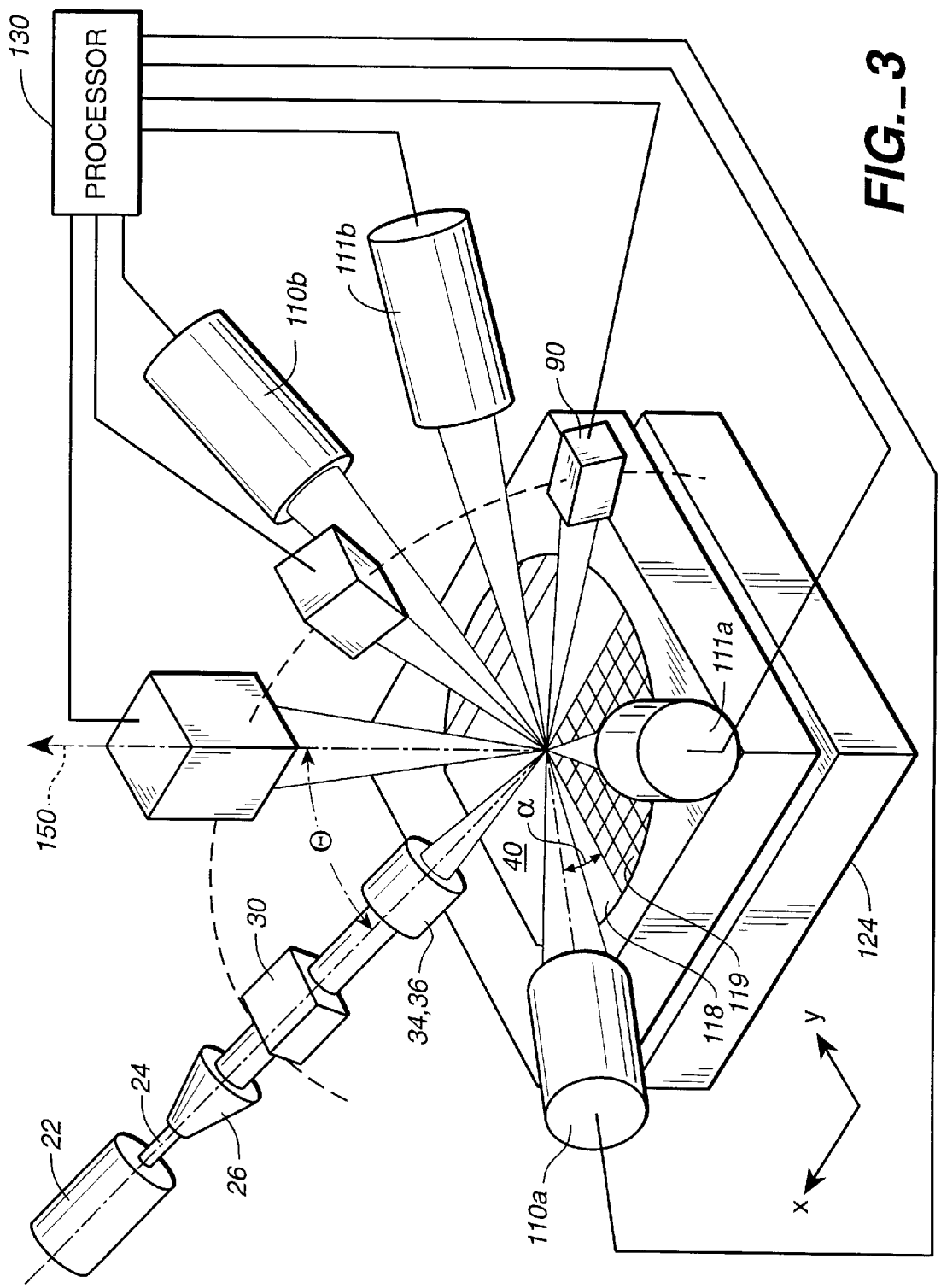
FIG._3

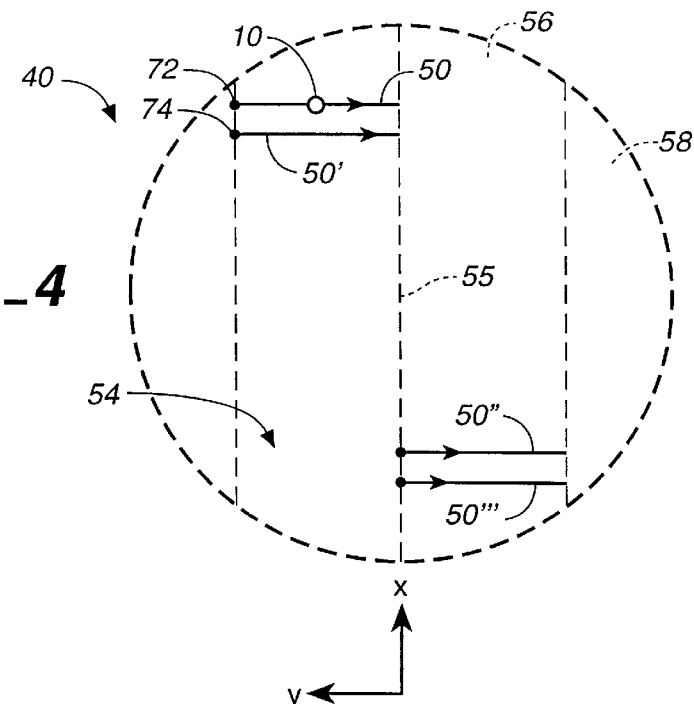
FIG._4
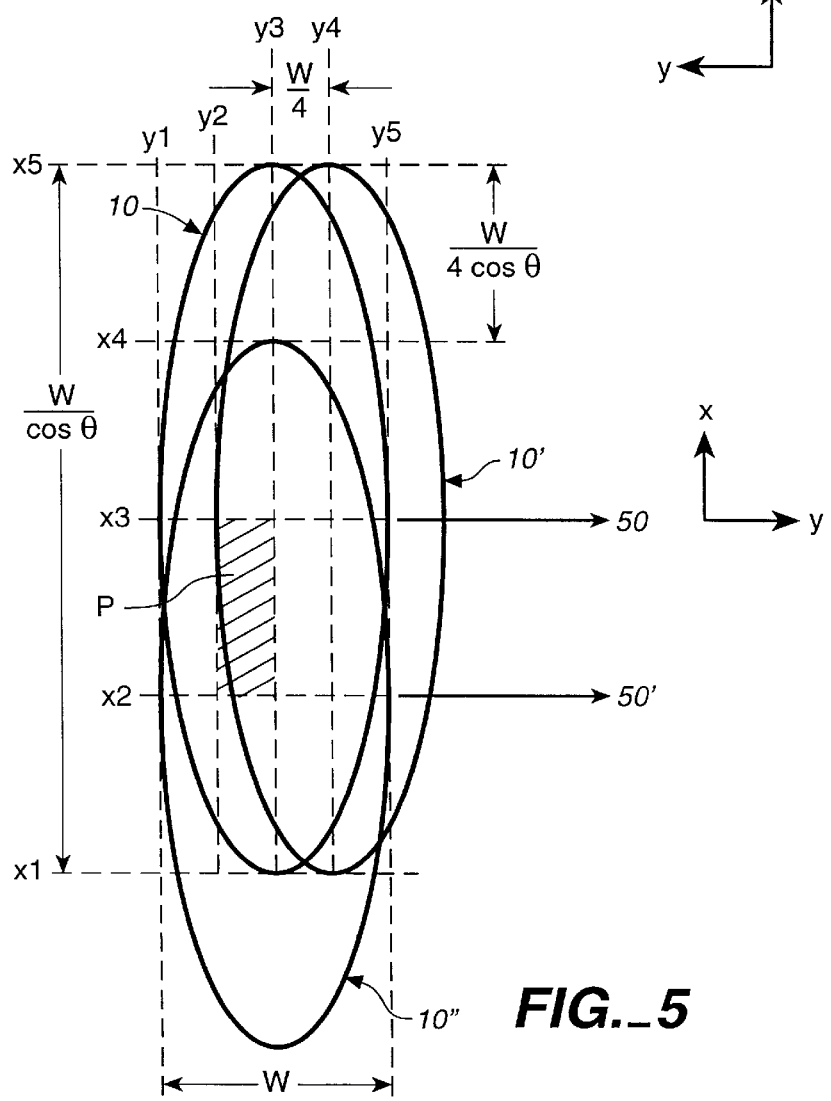
FIG._5

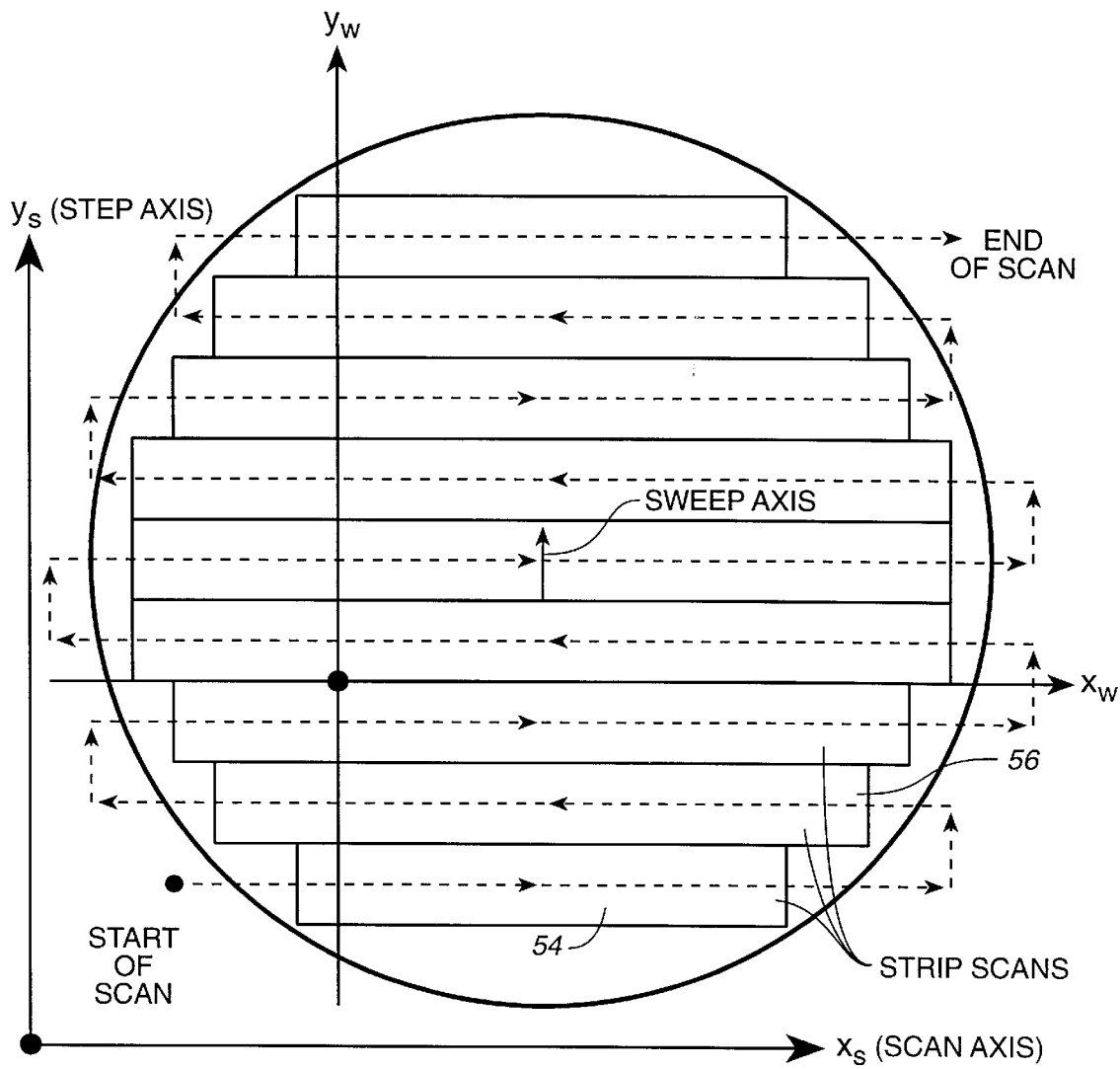
FIG._6

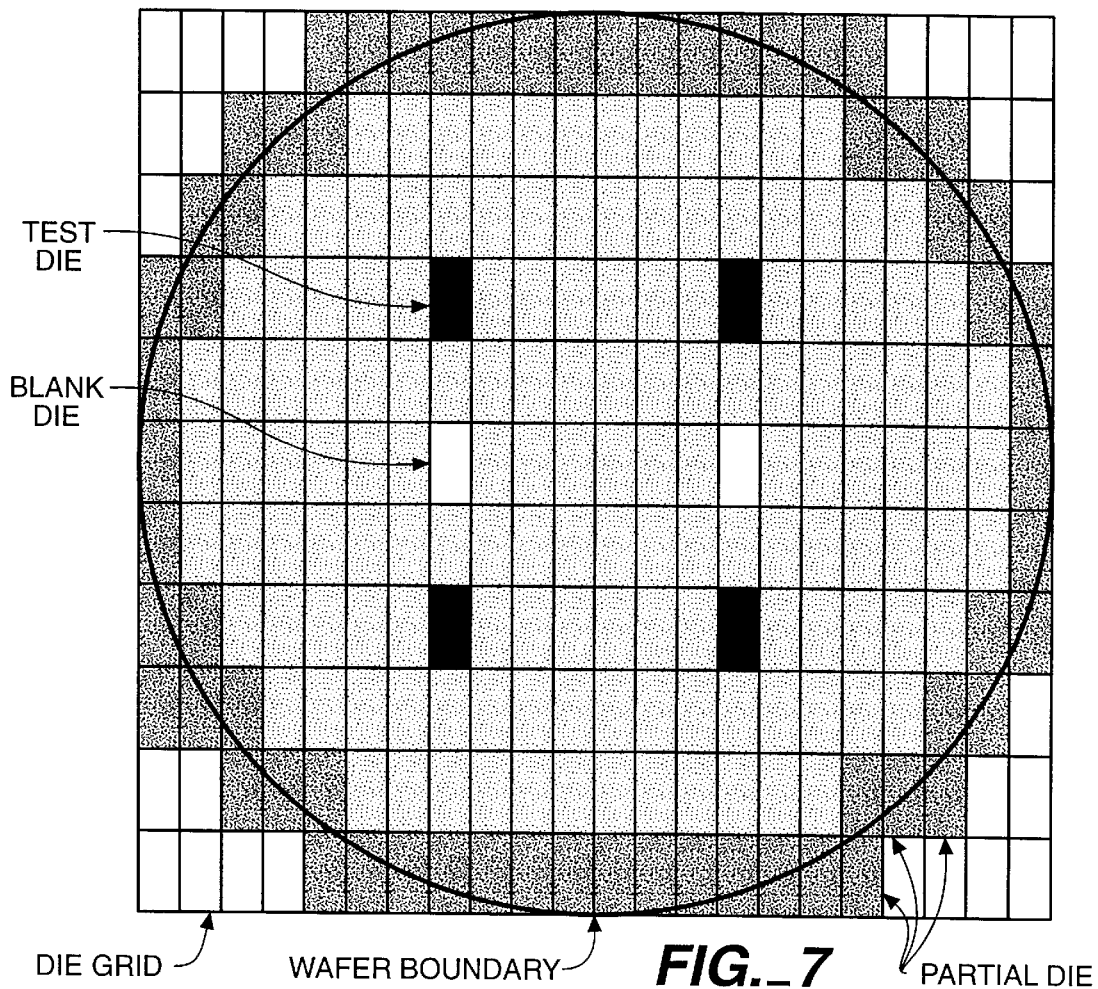
FIG._7
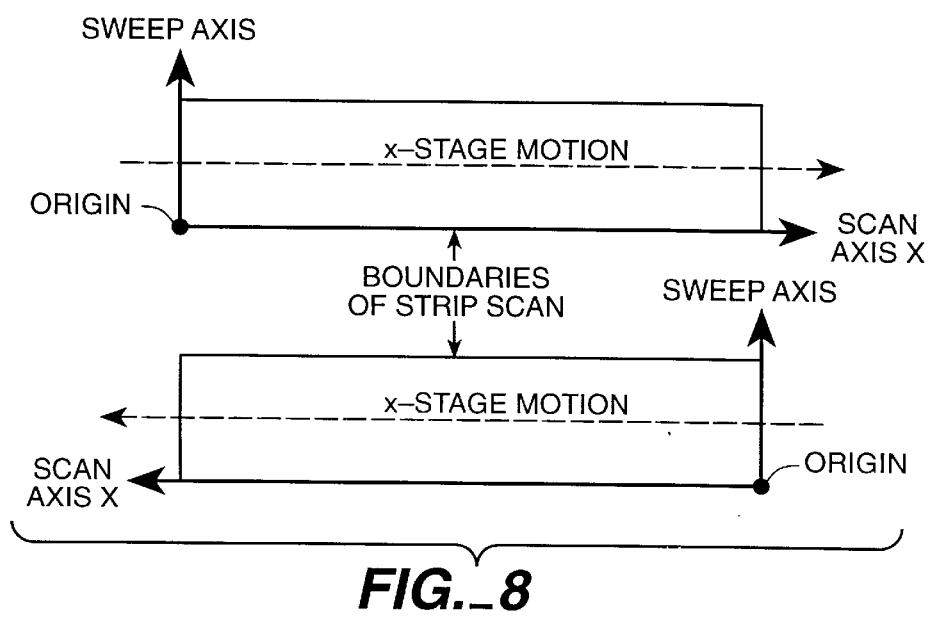
FIG._8

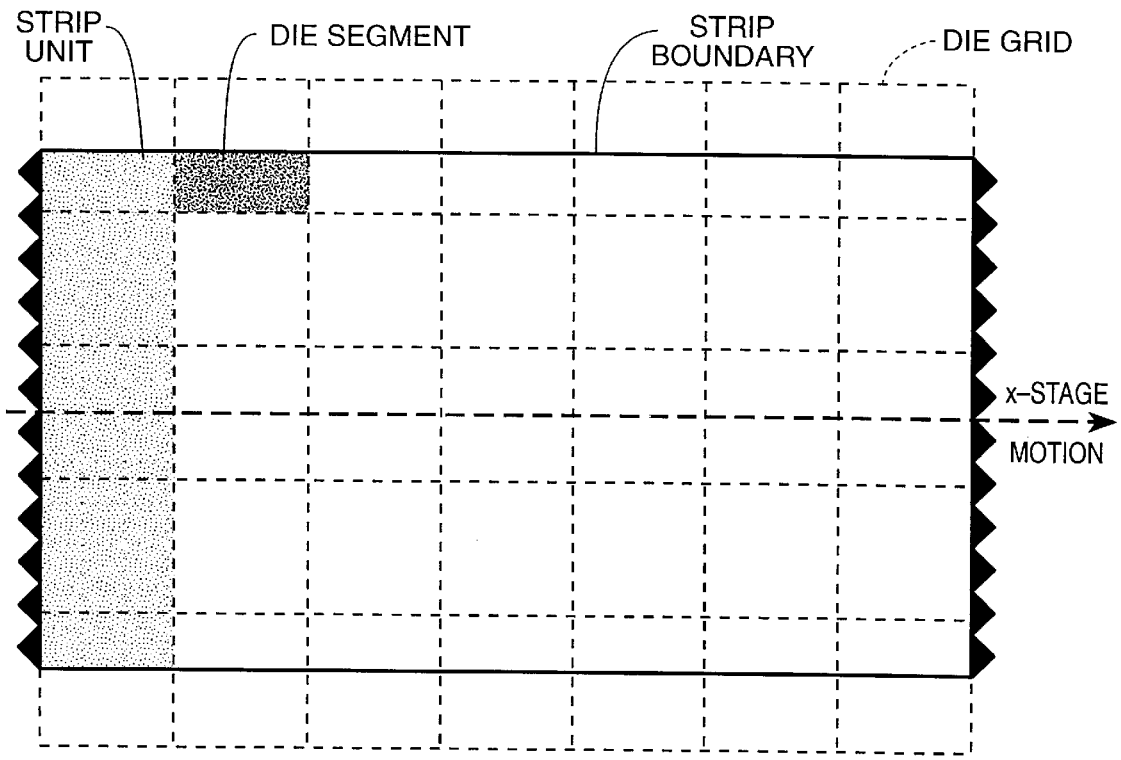
FIG._9
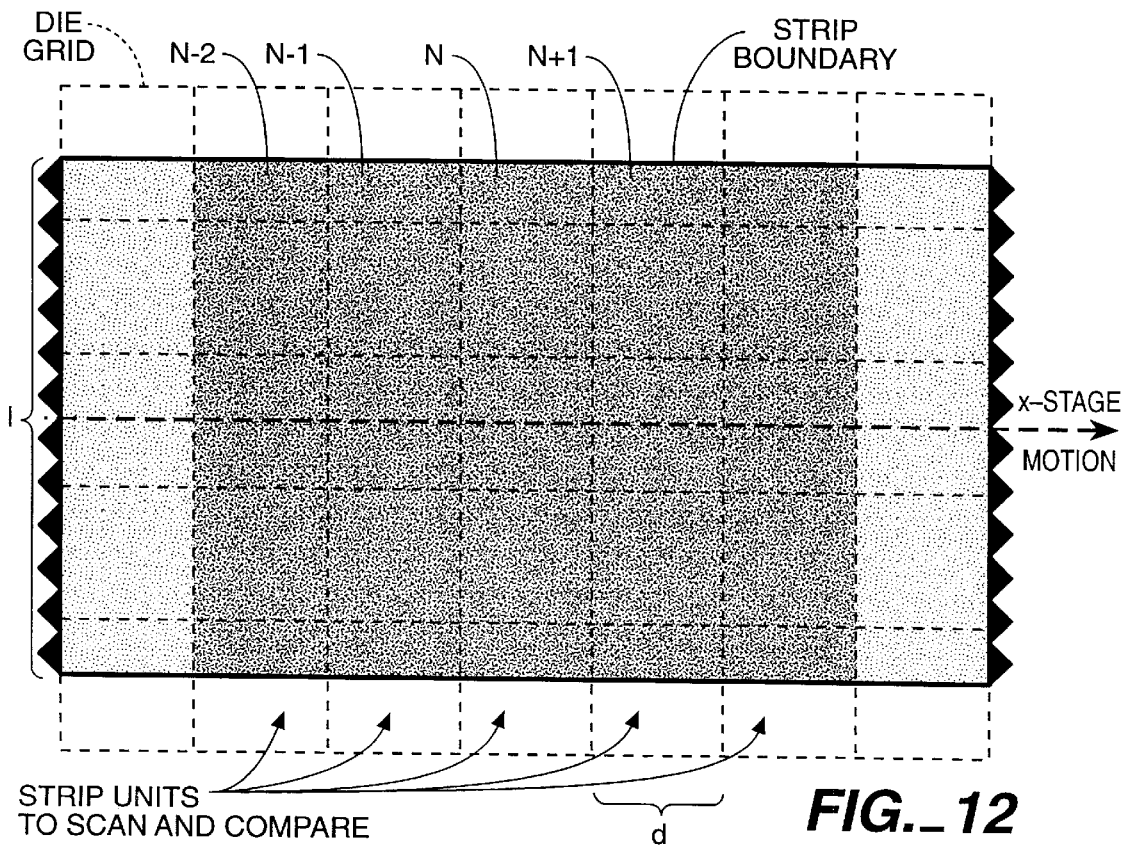
FIG._12

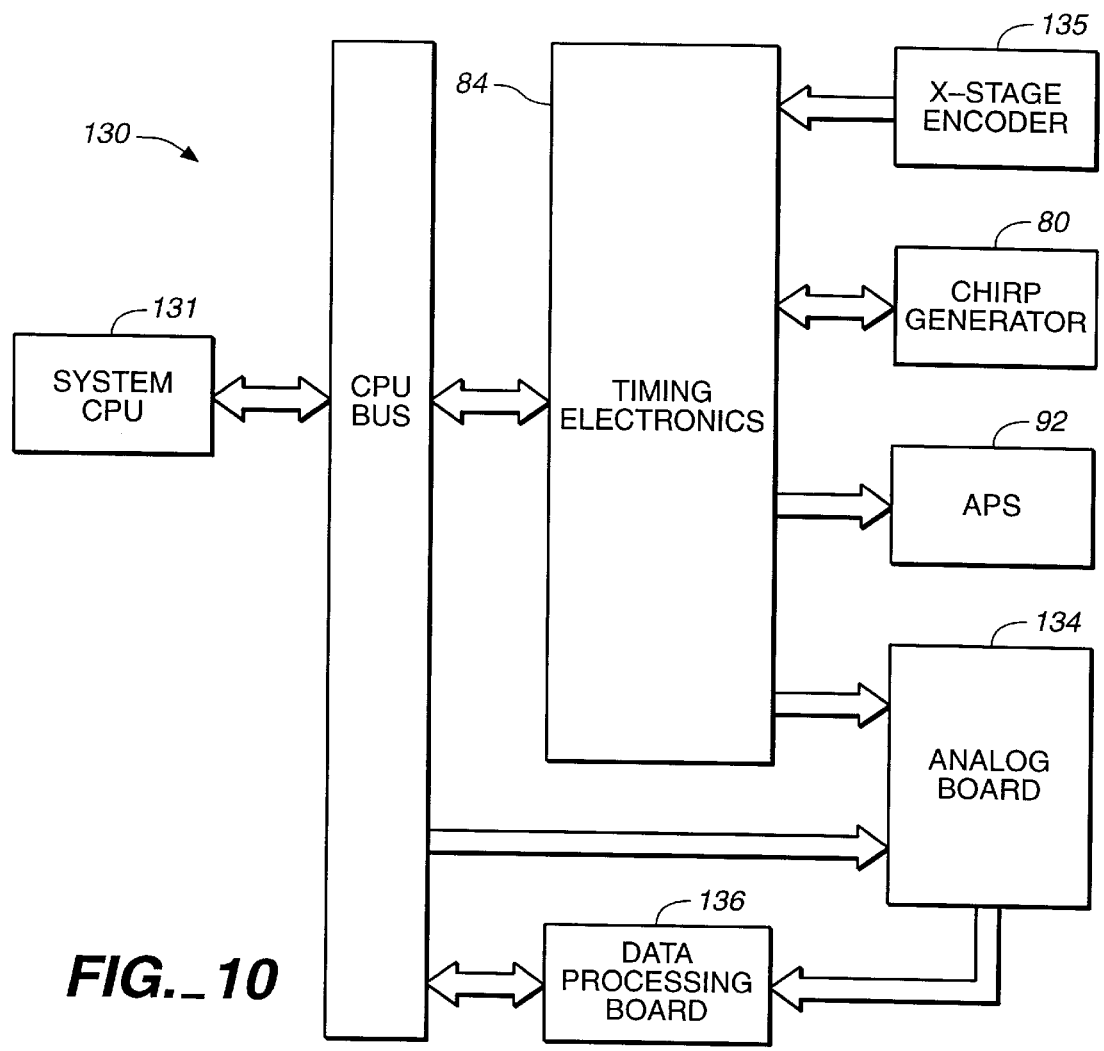
FIG._10
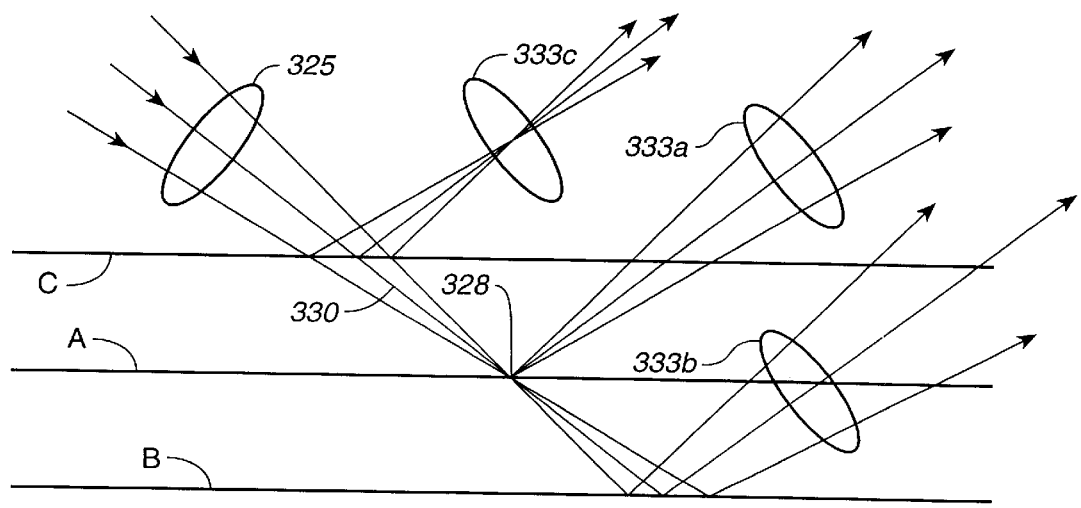
FIG._16

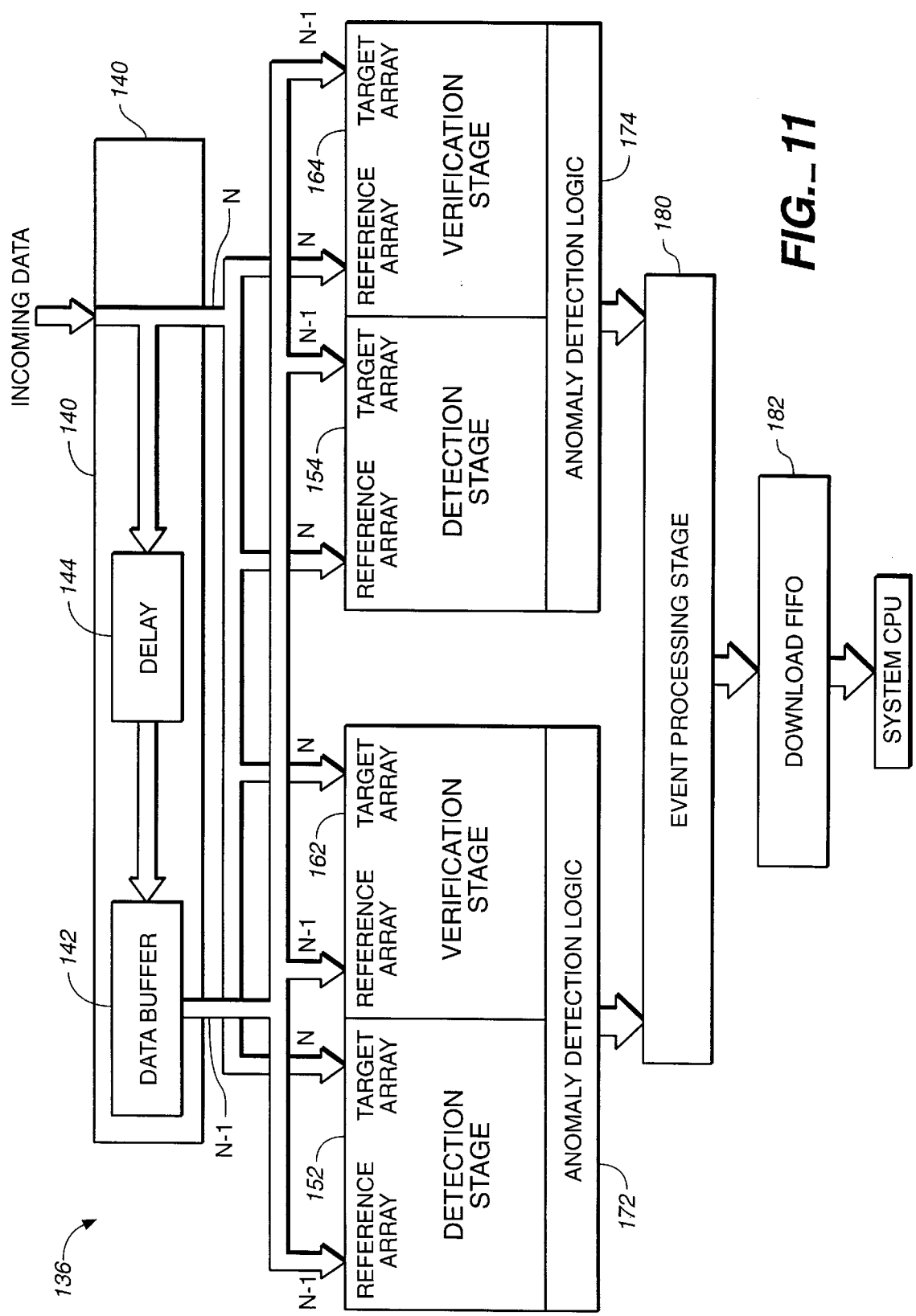
FIG._11

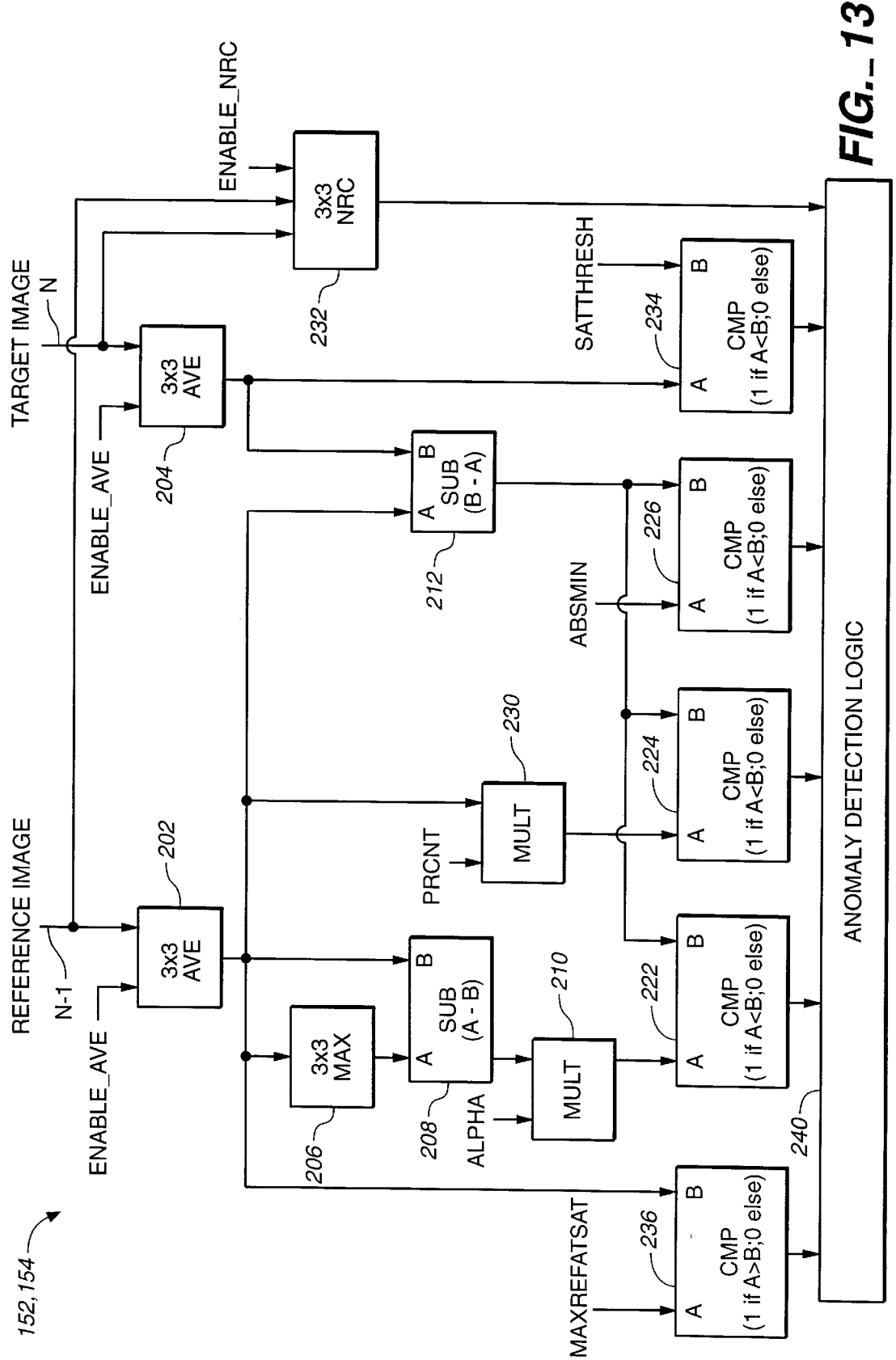
FIG._13

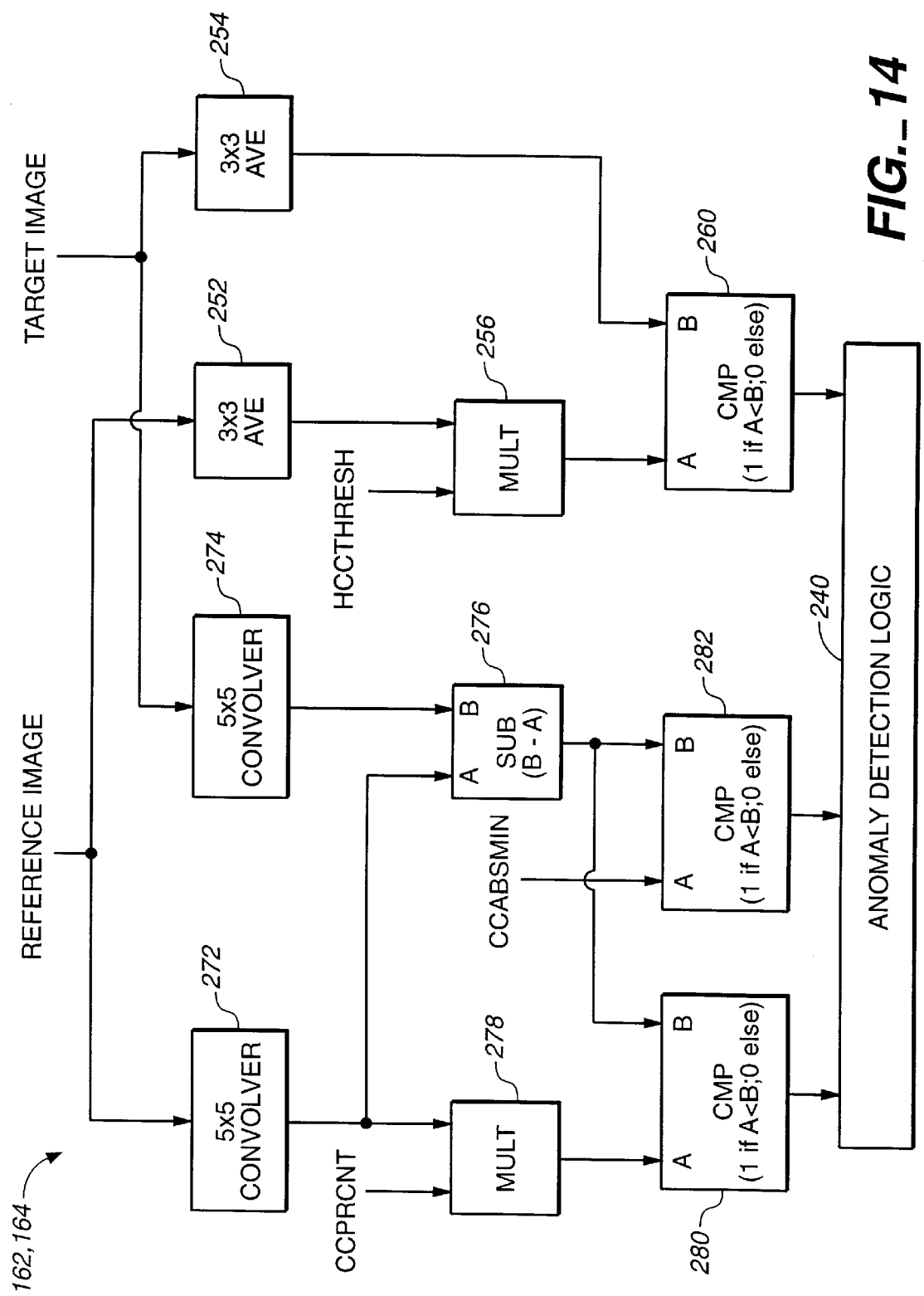
FIG._14

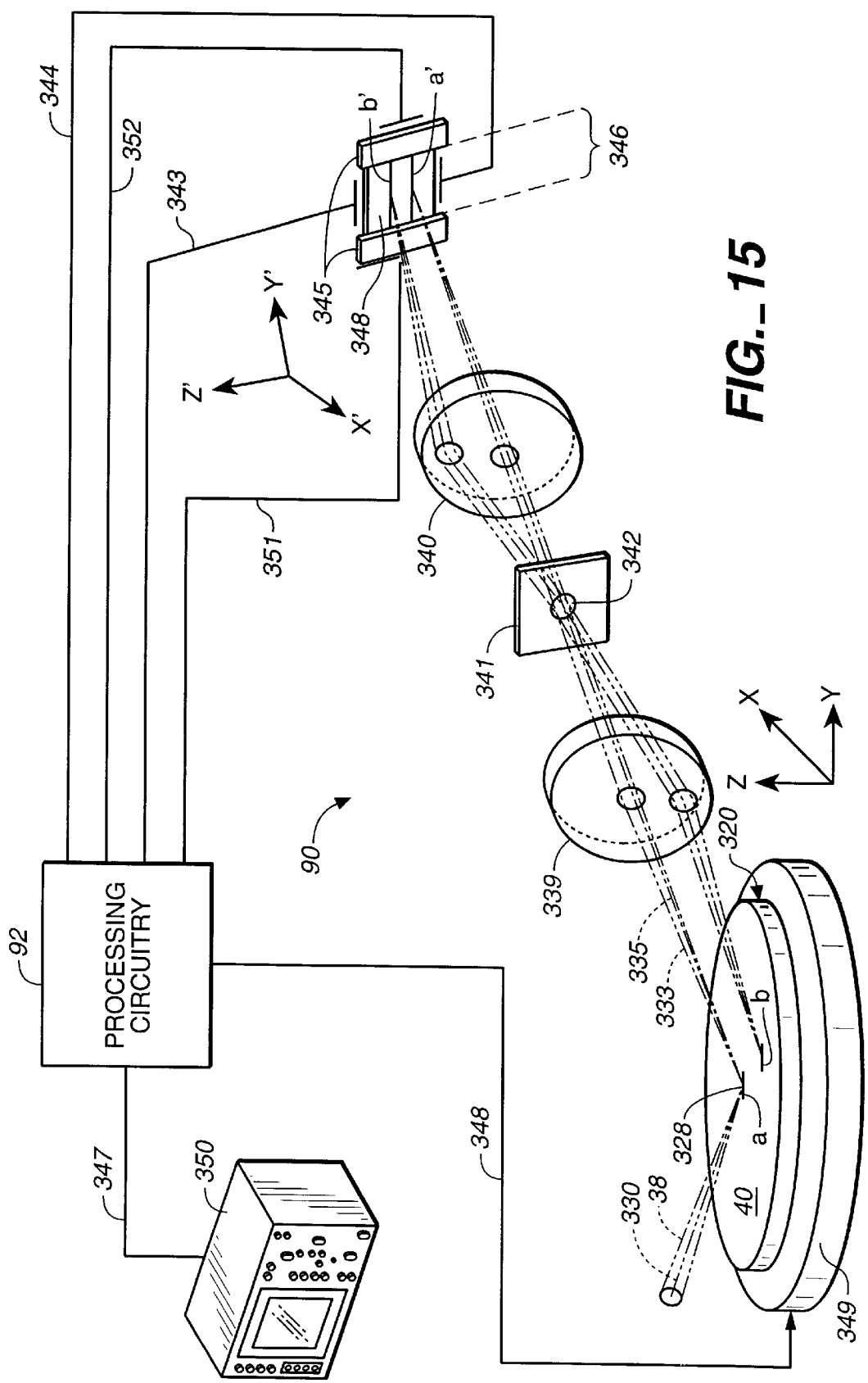
FIG._15

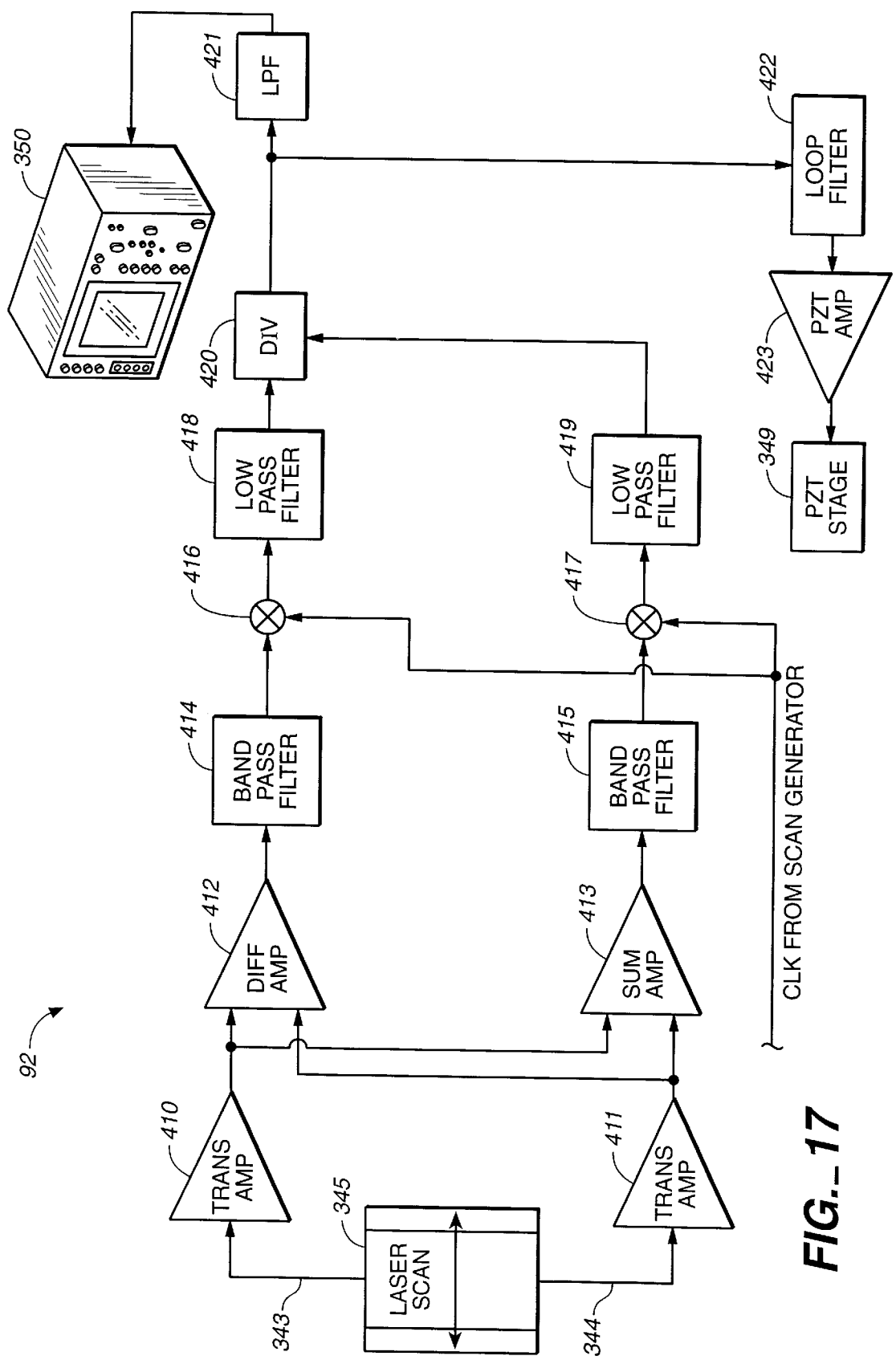
FIG._17

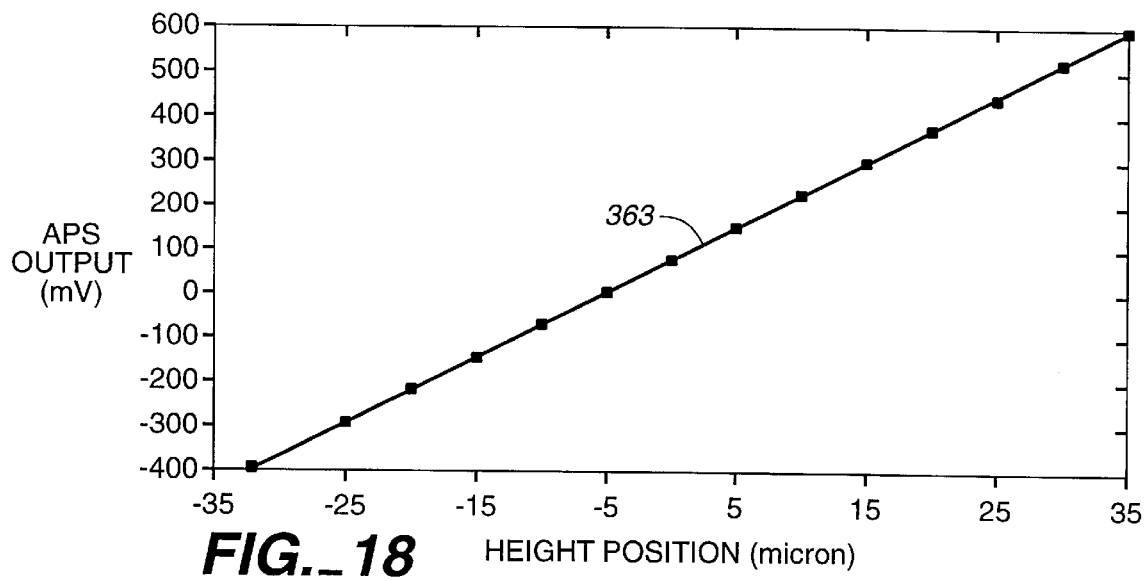
FIG._18
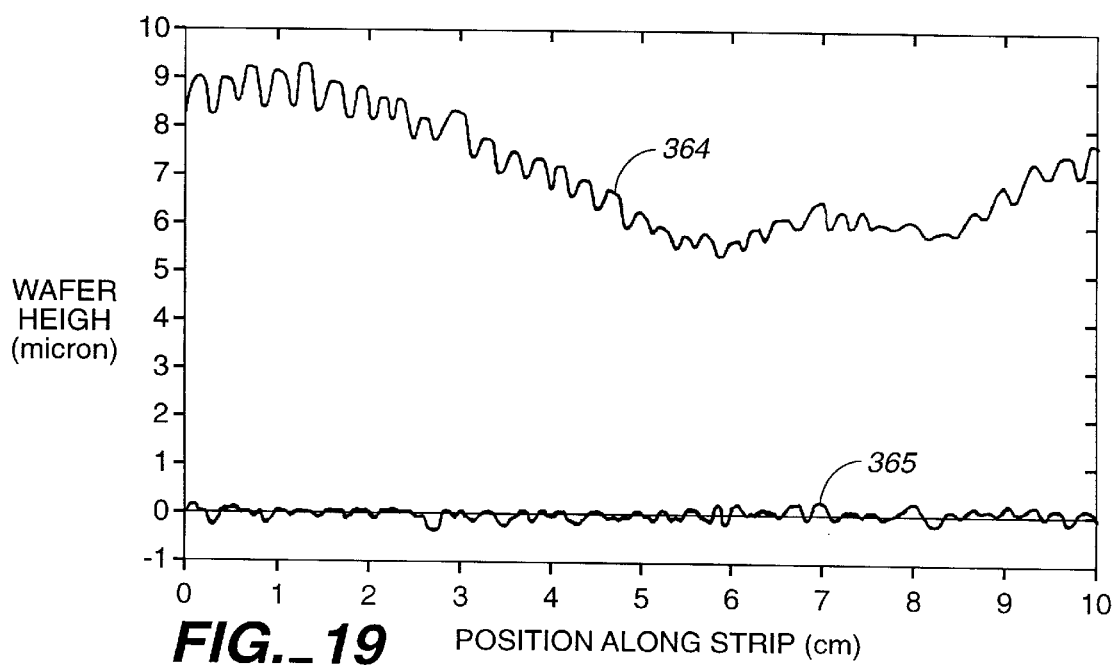
FIG._19

//  5,864,394

SURFACE INSPECTION SYSTEM

CROSS-REFERENCE TO RELATED APPLICATION

This application is a continuation-in-part application of the following parent applications:

1. "Wafer Alignment Sensor," by Mehrdad Nikoonahad and James A. Tebelskis, Ser. No. 08/263,203, filed Jun. 20, 1994 Pat. No. 5,576,831.

2. "Optical Scanning System for Surface Inspection," by Mehrdad Nikoonahad, Keith B . Wells, and Brian C. Leslie, Ser. No. 08/351,664 filed Dec. 8, 1994 now abandoned.

3. "Optical Wafer Positioning System," by Mehrdad Nikoonahad, Philip R. Rigg, Keith B. Wells, and David S. Calhoun, Ser. No. 08/361,131 filed Dec. 21, 1994 now U.S. Pat. No. 5,530,550.

4. "Scanning System for Inspecting Anomalies on Surfaces," by Mehrdad Nikoonahad and Stanley E. Stokowski, Ser. No. 08/499,995 filed Jul. 10, 1995 still pending.

MICROFICHE APPENDIX

Attached herewith as part of this application is a microfiche appendix including the following three items:

(1) "Patent Disclosure: SFS8000 Data Processing Algorithms, John Jordan, Sep. 11, 1995, pages 1–22;

(2) SFS8000 block diagrams—10 pages; and (3) Schematic circuit diagrams of 30 pages.

BACKGROUND OF THE INVENTION

This invention relates in general to surface inspection systems, and in particular, to a high speed scanner system for inspecting anomalies (contaminant particles and pattern defects) on surfaces. In particular, it relates to a surface inspection system for inspecting anomalies on substantially planar surfaces such as those of semiconductor wafers, photomasks, reticles, ceramic tiles, and other surfaces.

The size of semiconductor devices fabricated on silicon wafers has been continually reduced. At the time that this application is filed, for example, semiconductor devices can be fabricated at a resolution of a half micron or less, and sixty-four (64) megabits DRAMs are being fabricated with a 0.35 micron design rule. The shrinking of semiconductor devices to smaller and smaller sizes has imposed a much more stringent requirement on the sensitivity of wafer inspection instruments which are called upon to detect contaminant particles and pattern defects that are small compared to the size of the semiconductor devices. At the same time, it is desirable for wafer inspection systems to provide an adequate throughput so that these systems can be used for in-line inspection to detect wafer defects.

In U.S. Pat. No. 4,898,471 to Stonestrom et al. assigned to the present assignee of this application, the area illuminated on a wafer surface by a scanning beam is an ellipse which moves along a scan line henceforth called a sweep. In one example given by Stonestrom et al., the ellipse has a width of 20 microns and a length of 115 microns. Light scattered by anomalies or patterns in such illuminated area is detected by photodetectors placed at azimuthal angles in the range of 80° to 100°. The signals detected by the photodetectors are used to construct templates. When the elliptical spot is moved along the scan line to a neighboring region, scattered light from structures within the spot is again detected and the photodetector signal is then compared to a template to ascertain the presence of contaminant particles or pattern defects as opposed to regular pattern. In Stonestrom et al., the scanning beam scans across the entire wafer during each sweep, illuminating and inspecting the wafer, while the wafer is simultaneously moved by a mechanical stage in a direction substantially perpendicular to the sweep direction. This operation is then repeated until the entire wafer has been inspected.

While the system of Stonestrom et al. performs well for inspecting wafers having semiconductor devices that are fabricated with coarser resolution, with the continual shrinking of the size of the devices fabricated, it is now desirable to provide an improved inspection tool that can be used to detect very small anomalies that may be difficult to detect using Stonestrom et al.'s system.

Another type of surface inspection system is an imaging system that illuminates a large area and scans duplicate areas of surfaces, such as those of photomasks or semiconductor wafers. Optically scanned information from the duplicate areas is then compared to determine differences therebetween. As examples of such systems, see U.S. Pat. Nos. 4,532,650; 4,579,455; 4,805,123 and 4,926,489. In such systems, where the pixel is submicron in size, the optical scanning system requires significant time to scan the entire surface of a photomask or semiconductor wafer so that the throughput of such systems is typically low and usually not suitable for in-line inspection.

It is therefore desirable to provide an improved surface inspection system with adequate sensitivity for detecting small particles while achieving an adequate throughput at reasonable cost so that these systems can be used for in-line inspection to detect wafer defects.

SUMMARY OF THE INVENTION

The above-described desirable result is achieved by a number of features which may be used together or separately, or in various different combinations thereof. First the size of the area that is illuminated by the scanning light beam is chosen to be smaller than that in the Stonestrom, et al. patent referenced above to increase detection sensitivity. The size of the illuminated area or spot is not, however, so small as to prevent an adequate throughput. The number of samples (and therefore the number of pixels) taken within the illuminated area or spot is also not so large as to prevent an adequate throughput. In such manner, a surface inspection system with enhanced detection sensitivity, adequate throughput, and reasonable cost is achieved.

In the system of this invention, anomalies of an object to be inspected are preferably detected by comparing the optically scanned information (henceforth denoted images) of two adjacent patterns of a plurality of real or virtual repeating patterns on its surface. The image of a repeating pattern on the surface for which anomaly detection and verification are performed is denoted a target image, and the image of a repeating pattern on the surface that is adjacent to the target image is denoted a reference image. The comparison is preferably carried out by comparing the intensity of a first pixel location in the target image to that of a second pixel location in the reference image. The second pixel location is preferably located relative to the reference image in the same way as the first pixel location is located relative to the target image, so that if the target and reference images are placed one on top of the other, the first and second pixel locations would substantially overlap. Other spatial relationships may also be defined between the first and second pixel locations. For each pixel location in the target image, a corresponding pixel location may be defined in the reference image that has the above-described spatial relationship to each such pixel location in the target image.

By choosing an illumination spot size which is smaller than that of Stonestrom, et al., a problem may arise in the detection by comparison if the images of the two adjacent patterns are misregistered. By employing precise system design and correcting the height of the surface during the inspection process, the misregistration error is reduced to an extent that greatly simplifies the comparison process. Efficient data comparison can then be used for the detection and verification of anomalies.

Instead of comparing images of adjacent patterns on a surface, the system of this invention is also useful for detecting anomalies by comparing a target image to a reference image that is not from a repeating pattern on the surface. Such and other applications are within the scope of the invention.

One aspect of the invention is directed towards an inspection system for detecting anomalies on a surface, comprising means for optically scanning the surface; means for collecting light scattered by the surface and deriving an intensity value for at least a first pixel location from the collected light, and means for determining an error threshold for said at least first pixel location from intensity values stored for a corresponding second pixel location and its neighboring pixel locations of a reference image of the surface. The error threshold is determined by the maximum difference of intensity values stored for the second pixel location and its neighboring pixel locations of the reference image. The system further comprises means for identifying anomalies by comparing the difference between the intensity value for the at least first pixel location and that stored for the second pixel location to said error threshold.

Another aspect of the invention is directed towards an inspection system for detecting anomalies on a surface, comprising means for optically scanning the surface, means for collecting light scattered by the surface and deriving intensity values for at least a first pixel location and its adjacent pixel locations from the collected light, and a memory storing an intensity value for a second pixel location of a reference image of the surface. The second pixel location corresponds in position to the at least first pixel location. The memory also stores intensity values for neighboring pixel locations of the second pixel in the reference image. These pixel locations correspond in position to the adjacent pixel locations of the at least first pixel location. The system further includes means for identifying anomalies by ascertaining whether some of the intensity values for the first pixel location and its adjacent pixel locations exceed those stored for the corresponding second pixel location and its neighboring pixel locations.

Still another aspect of the invention is directed towards an inspection system for verifying the anomaly on a surface, comprising means for providing the intensity value for a least a first pixel location on the surface, a memory storing an intensity value for a second pixel location of a reference image of the surface, said second pixel location corresponding in position to the at least first pixel location, and means for verifying the anomaly by ascertaining whether the intensity value of the at least first pixel location is a multiple of the intensity value of the second pixel location, where the multiple is in the range of 2–16.

Yet another aspect of the invention is directed towards an inspection system for verifying an anomaly on a surface, comprising means for providing the intensity values for at least a first pixel location and its adjacent pixel locations on the surface, and a memory storing an intensity value for a second pixel location of a reference image of the surface, said second pixel location corresponding in position to the at least first pixel location, and storing intensity values for neighboring pixel locations of the second pixel in the reference image corresponding in position to the adjacent pixel locations of the at least first pixel location. The system further includes means for verifying the identified anomaly by convolving a convolution matrix with the intensity values at said first pixel location and its adjacent pixel locations to obtain a first convolved value, and with the intensity values at said second pixel location and its neighboring pixel locations to obtain a second convolved value, and determining whether the difference between the first and second convolved values exceeds a predetermined convolution threshold.

One more aspect of the invention is directed towards an inspection method for detecting anomalies on a surface, comprising the steps of: optically scanning the surface; collecting light scattered by the surface and deriving an intensity value for at least a first pixel location from the collected light; determining an error threshold for said at least first pixel location from intensity values stored for a corresponding second pixel location and its neighboring pixel locations of a reference image of the surface. The error threshold is determined by the maximum difference of intensity values stored for the second pixel location and its neighboring pixel locations of the reference image. The method further comprises identifying anomalies by comparing the difference between the intensity value for the at least first pixel location and that stored for the second pixel location to said error threshold.

Another aspect of the invention is directed towards an inspection method for detecting anomalies on a surface, comprising the steps of: optically scanning the surface, collecting light scattered by the surface, and deriving intensity values for said first pixel location and for its adjacent pixel locations from the collected light; storing intensity values for a second pixel location of a reference image of the surface, said second pixel location corresponding in position to the at least first pixel location, and for neighboring pixel locations of the second pixel in the reference image corresponding in position to the adjacent pixel locations of the at least first pixel location. The method further comprises identifying anomalies by ascertaining whether some of the intensity values for the first pixel location and its adjacent pixel locations exceed those stored for the corresponding second pixel location and its neighboring pixel locations.

One more aspect of the invention is directed towards an inspection method for verifying an anomaly on a surface, comprising the steps of: providing the intensity value for at least a first pixel location on a surface; storing an intensity value for a second pixel location of a reference image of the surface, said second pixel location corresponding in position to the at least first pixel location; and verifying the anomaly by ascertaining whether the intensity value of the at least first pixel location is a multiple of the intensity value of the second pixel location, where the multiple is in the range of 2–16.

One more aspect of the invention is directed towards an inspection method for verifying an anomaly on a surface, comprising the steps of: providing the intensity values for at least a first pixel location and its adjacent pixel locations on a surface; storing intensity values for a second pixel location of a reference image of a surface, said second pixel location corresponding in position to the at least first pixel location, and for neighboring pixel locations of the second pixel in the reference image corresponding in position to the adjacent pixel locations of the at least first pixel location. The method further comprises verifying the identified anomaly by convolving a convolution matrix with the intensity values at said first pixel location and its adjacent pixel locations to obtain a first convolved value, and with the intensity values at said second pixel location and its neighboring pixel locations to obtain a second convolved value, and determining whether the difference between the first and second convolved values exceeds a predetermined convolution threshold.

Still one more aspect of the invention is directed towards a system for detecting anomalies on a surface, comprising means for directing a focused beam of light at a grazing angle toward said surface, means for causing relative motion between the beam and the surface so that the entire surface is scanned with said beam; and means for detecting the specular reflection from the surface and dynamically measuring the height of the surface during a scan. The system further comprises means for dynamically correcting the height of the surface during a scan, means for collecting light scattered from the surface and converting such light into an electrical signal, and means for digitally processing said electrical signal for detecting anomalies.

One more aspect of the invention is directed towards a method for detecting anomalies on a surface, comprising the steps of directing a focused beam of light at a grazing angle toward said surface, causing relative motion between the beam and the surface so that the entire surface is scanned with said beam, detecting the specular reflection from this surface and dynamically measuring the height of the surface during a scan. The method further comprises dynamically correcting the height of the surface during a scan, collecting light scattered from the surface, converting such light into an electrical signal, and digitally processing the electrical signal for detecting anomalies.

Still another aspect of the invention is directed towards a method for detecting anomalies on a surface of a semiconductor wafer, comprising the following steps: directing a focused beam of light towards said surface to illuminate an area of the surface defining a spot; causing relative motion between the beam and the wafer so that the beam scans a serpentine path covering substantially the entire surface; and collecting scattered light for detecting anomalies and converting collected light into an electrical signal. The spot size and directing and causing steps are such that the beam substantially inspects the entire surface of the wafer at a throughput in excess of about 40 wafers per hour for 150 mm diameter wafers, at a throughput in excess of about 20 wafers per hour for 200 mm diameter wafers, and at a throughput in excess of about 10 wafers for per hour for 300 mm diameter wafers. The method further comprises digitally processing the electrical signal for detecting anomalies at a data clock rate of less than 50 megahertz.

Yet another aspect of the invention is directed towards a method for detecting anomalies on a surface, comprising the steps of: directing a focused beam of light towards said surface to illuminate an area of the surface defining a spot; causing relative motion between the beam and the surface so that the beam scans a serpentine path covering substantially the entire surface, collecting scattered light for detecting anomalies and converting the collected light into an electrical signal. The spot size and the directing and causing steps are such that the surface is inspected at a speed of not less than about 1.5 cm$^2$/s. The method further comprises digitally processing the electrical signal for detecting anomalies at a data clock rate of less than 50 megahertz.

One more aspect of the invention is directed towards a method for detecting anomalies on a surface comprising the directing, causing, and collecting and converting steps of the immediately preceding paragraph. The surface has dimensions of not less than 200 mm in any direction along the surface, wherein said directing and causing steps are such that the beam scans substantially the entire surface in about 50–90 seconds. The method further comprises the digital processing step of the immediately preceding paragraph.

Yet another aspect of the invention is directed towards a method for detecting anomalies on a surface, comprising the steps of: directing a focused beam of light towards said surface to illuminate an area of the surface defining a spot whose size is in the range of about 5–15 micrometers; causing relative motion between the beam and the surface so that the beam scans a serpentine path covering substantially the entire surface; and collecting scattered light for detecting anomalies and converting the collected light into an electrical signal. The method further comprises digitally processing said electrical signal for detecting anomalies at a data clock rate of less than 50 megahertz.

Still one more aspect of the invention is directed towards a system for detecting anomalies on a surface, comprising means for directing a focused beam of light towards said surface at an oblique angle of $\Theta$ from the normal direction to the surface to the plurality of areas on a surface during the scan. Each such illuminated area on the surface defines a spot size of w. The system further comprises means for causing relative motion between the beam and the surface so that the beam scans a serpentine path covering substantially the entire surface. The path includes a plurality of strips of sweeps of effective length l shorter than the dimensions of the surface, where the beam sweeps with a frequency of 1/T (T including overhead time associated with each sweep). The system further comprises means for collecting scattered light for detecting anomalies and converting the collected light into electrical signals representing light collected from N pixels within each spot, and means for digitally processing said electrical signal for detecting anomalies, at an average data clock rate substantially proportional to Nl/wT.

BRIEF DESCRIPTION OF THE DRAWINGS

FIG. 1A is a schematic view of an elliptical-shaped illuminated area or spot on a surface to be inspected to illustrate the invention.

FIG. 1B is a graphical illustration of the illumination intensity across the width or short axis of the elliptical spot of FIG. 1A for defining a boundary of the spot and to illustrate the invention.

FIG. 2 shows partially in perspective and partially in block diagram form a system for inspecting anomalies of a semiconductor wafer surface to illustrate the preferred embodiment of the invention.

FIG. 3 is a perspective view showing in more detail the illumination and collection features of the system of FIG. 2.

FIG. 4 is a schematic view of a small portion of a semiconductor wafer surface illustrating the scan path of an illumination spot on the surface to illustrate the preferred embodiment.

FIG. 5 is a schematic view of three elliptical illuminated areas or spots to illustrate the scanning and data acquisition processes of this invention.

FIG. 6 is a schematic diagram of a semiconductor wafer and a serpentine scan path to illustrate the intensity value data acquisition process.

FIG. 7 is a schematic view of a patterned wafer surface to illustrate the invention.

FIG. 8 is a schematic diagram of sweep and (mechanical) scan axes to further illustrate the data acquisition process.

FIG. 9 is a schematic view of a portion of a patterned wafer surface illustrating the intersection of a strip unit with a die grid to illustrate the data processing portion of the system of this invention.

FIG. 10 is a functional block diagram of the data processing subsystem of the present system of the invention.

FIG. 11 is a functional block diagram of the data processing board portion of the subsystem of FIG. 10 to illustrate the preferred embodiment of the invention.

FIG. 12 is a schematic view illustrating a portion of a patterned wafer surface illustrating a number of strip units and the anomaly detection and verification processes.

FIG. 13 is a block diagram of each of the two detection stages of FIG. 11 to illustrate the preferred embodiment of the invention.

FIG. 14 is a block diagram of each of the two verification stages of FIG. 11 to illustrate the preferred embodiment of the invention.

FIG. 15 is a diagram of a surface positioning system of the present invention for particle detection on a surface.

FIG. 16 is a side view of a beam reflecting from a surface at various height positions in accord with the present invention.

FIG. 17 is a block diagram of the processing circuitry shown in FIG. 15.

FIG. 18 is a graphical representation of an electrical signal amplitude versus the height position of the surface shown in FIG. 15 of the present invention.

FIG. 19 is a graphic representation of wafer height along a strip of the wafer surface.

For simplicity, identical components in the different figures of this invention are labeled by the same numerals.

DETAILED DESCRIPTION OF THE PREFERRED EMBODIMENTS

FIG. 1A is a schematic view of an elliptical-shaped illuminated area (or spot) of a surface inspected by the system of this invention to illustrate the invention. As explained below, the laser beam illuminating the surface inspected approaches the surface at a grazing angle, so that even though the illumination beam has a generally circular cross-section, the area illuminated is elliptical in shape such as area 10 in FIG. 1A. As known to those skilled in the art, in light beams such as laser beams, the intensity of the light typically does not have a flat distribution and does not fall off abruptly to zero across the boundary of the spot illuminated, such as at boundary 10a of spot 10 of FIG. 1A. Instead, the intensity falls off at the outer edge of the illuminated spot at a certain inclined slope, so that instead of sharp boundaries such as boundary 10a illustrated in FIG. 1A, the boundary is typically blurred and forms a band of decreasing intensity at increasing distance away from the center of the illuminated area.

In many lasers, the laser beam produced has a Gaussian intensity distribution, such as that shown in FIG. 1B. FIG. 1B is a graphical illustration of the spatial distribution of the illumination intensity in the Y direction of a laser beam that is used in the preferred embodiment to illuminate spot 10 of a surface to be inspected as shown in FIG. 1A, and thus is also the illumination intensity distribution across spot 10 in the Y direction. As shown in FIG. 1B, the illumination intensity has been normalized so that the peak intensity is 1, and the illumination intensity has a Gaussian distribution in the X direction as well as in the Y direction. Points 12 and 14 are at spatial locations y1 and y5 at which points the illumination intensity drops to $1/e^2$ of the peak intensity, where e is the natural number. As used herein to describe the preferred embodiment, the minimum width of spot 10 is the distance between these two points (distance between y1 and y5); this distance is the length of the short axis of the elliptical illuminated area 10 and is denoted as the width w in FIG. 1A. The spot 10 is defined by the area within a boundary 10a where the illumination is $1/e^2$ of that of the maximum intensity of illumination at the center of the spot.

As a broader definition, "minimum width" of the elliptical spot 10a may be defined as the minimum distance between two parallel lines that enclose between them the boundary of the area or spot. In reference to spot 10 in FIG. 1A, for example, if one were to draw two parallel lines enclosing the boundary 10a, such as lines q1, q2, the distance between lines q1, q2 is d, which is minimized when both q1, q2 touch the boundary 10a. The distance d is minimum for all directions of q1, q2 when the lines q1, q2 coincide with grid lines x1, x5, so that the minimum width of the spot 10 is w. Even where 10a is not an ellipse, but is of another shape such as rectangular, square, or irregular in shape, the same broader definition is applicable.

It should be noted that FIG. 1B shows only the main lobe of the spot illuminated by the laser or light beam. It is known that the main lobe is also accompanied by sidelobes, so that areas of the surface outside of area or spot 10 would also be illuminated; scattering by structures of the surface of the light in the sidelobes and collected by the detectors causes noise.

For a spot that is relatively small compared to the size of the surface to be inspected, it will be difficult to maintain uniformity of the spot across a sweep which spans the entire length or width of the wafer. In reference to FIGS. 1A, 1B, the variation in the minimum width (as defined above) w of the main lobe of the focal plane intensity distribution and the level of the sidelobes are measures of the uniformity of the spot 10 as the beam scans across the surface. Where the minimum width and the sidelobes level vary little over the sweep, the spot is said to be uniform. In other words, when the spot size is relatively small compared to the size of the surface to be inspected, it will be difficult to maintain uniform width of the main lobe and uniform level of the sidelobes of the focal plane intensity distribution throughout the extent of a long sweep across the entire width of the wafer. A variation in either one of these two parameters (width of main lobe, sidelobe level) leads to a variation in detection sensitivity along the sweep which is undesirable.

These problems are solved in the surface inspection system of this application where the size of the area illuminated by the scanning light beam can be reduced while maintaining uniform detection sensitivity by causing the scanning light beam to scan short sweeps having a spatial span less than the dimension of the surface it is scanning, as illustrated in the preferred embodiment in FIGS. 2 and 4, where these short sweeps are not connected together but are located so that they form arrays of sweeps as illustrated in more detail below.

The surface inspection system of this application will now be described in reference to FIGS. 2 and 3. As shown in FIG. 2, system 20 includes a laser 22 providing a laser beam 24. Beam 24 is expanded by beam expander 26 and the expanded beam 28 is deflected by acousto-optic deflector (AOD) 30 into a defected beam 32. The deflected beam 32 is passed through post-AOD and polarization selection optics 34 and the resulting beam is focused by telecentric scan lens 36 onto a spot 10 on surface 40 to be inspected, such as that of a semiconductor wafer, photomask or ceramic tile, patterned or unpatterned.

In order to move the illuminated area that is focused onto surface 40 for scanning the entire surface, the AOD 30 causes the deflected beam 32 to change in direction, thereby causing the illuminated spot 10 on surface 40 to be scanned along a sweep 50. As shown in FIG. 2, sweep 50 is preferably a straight line having a length which is smaller than the dimension of surface 40 along the same direction as the sweep. Even where sweep 50 is curved, its span is less than the dimension of surface 40 along the same general direction. While the illuminated spot is scanning surface 40 along sweep 50, surface 40 of the wafer is moved by XY stage 124 along the X axis so that the illuminated area of the surface moves along arrow 52 and AOD 30 causes the illuminated spot to scan a sweep parallel to sweep 50 and in an adjacent position spaced apart from sweep 50 along the nagative X axis. As the illuminated spot covers said sweep, surface 40 is moved by a small distance so that the area of the surface to be illuminated is moved along direction 52 in order to scan an adjacent sweep at a different X position. As described below, this small distance is preferably equal to about one quarter of the dimension of spot 10 in the X direction. This process is repeated until the illuminated spot has covered strip 54; at this point in time the illuminated area is at or close to the edge 54a. At such point, the surface 40 is moved by XY stage 124 along the Y direction by about the length of sweep 50 in order to scan and cover an adjacent strip 56, beginning at a position at or close to edge 56a. The surface in strip 56 is then covered by short sweeps such as 50 in a similar manner until the other end or edge 56b of strip 56 is reached at which point surface 50 is again moved along the Y direction for scanning strip 58. This process is repeated prior to the scanning of strip 54, 56, 58 and continues after the scanning of such strips until the entire surface 40 is scanned. Surface 40 is therefore scanned by scanning a plurality of arrays of sweeps the totality of which substantially covers the entire surface 40.

FIG. 4 is an exploded view of a portion of the two strips 54, 56 and smaller portions of two other neighboring strips to illustrate in more detail the above-described scanning process. In the preferred embodiment as shown in FIG. 4, the optical beam 38 scans in only one direction as illustrated by the arrows of sweeps 50, 50', 50", 50'". Sweep 50 has an effective start location at 72 and spot 10 moves to the right therefrom until it reaches the border 55 between strips 54 and 56. As the spot traverses the sweep, a stage (see FIG. 3) moves the surface 40 in the direction substantially perpendicular to the sweep direction Y and the spot assumes the new start position 74 and moves along a sweep 50' parallel to sweep 50. The movement of the spot 10 along sweeps 50, 50', 50", 50'" and so on is achieved by means of AOD 30 as explained below.

The deflection of beam 32 by AOD 30 is controlled by chirp generator 80 which generates a chirp signal. The chirp signal is amplified by amplifier 82 and applied to the transducer portion of AOD 30 for generating sound waves to cause deflection of beam 32 in a manner known to those skilled in the art. For a detailed description of the operation of the AOD, see "Acoustooptic Scanners and Modulators," by Milton Gottlieb in *Optical Scanning,* ed. by Gerald F. Marshall, Dekker 1991, pp. 615–685. Briefly, the sound waves generated by the transducer portion of AOD 30 modulate the optical refractive index of an acoustooptic crystal in a periodic fashion thereby leading to deflection of beam 32. Chirp generator 80 generates appropriate signals so that after being focused by lens 36, the deflection of beam 32 causes the focused beam to scan along a sweep such as sweep 50 in the manner described.

Chirp generator 80 is controlled by timing electronic circuit 84 which in the preferred embodiment includes a microprocessor. The microprocessor supplies the beginning and end frequencies f1, f2 to the chirp generator 80 for generating appropriate chirp signals to cause the deflection of beam 32 within a predetermined range of deflection angles determined by the frequencies f1, f2. The autoposition sensor (APS) optics 90 and APS electronics 92 are used to detect the level or height of surface 40 and form a part of the Related Application. Detectors such as detectors 110a, 110b, 111a, 111b of FIGS. 2, 3 collect light scattered by anomalies as well as the surface and other structures thereon along sweep 50 and provide output signals to a processor 130 (which may be a set of processors, one for each detector) in order to detect anomalies and analyze their characteristics.

FIG. 3 is a perspective view of system 20 of FIG. 2 showing in more detail the arrangement of the collection/detection channels to illustrate the preferred embodiment. Surface 40 may be smooth (118) or patterned (119). The angle between the incident focused beam 38 and the normal direction 150 to the surface 40 is preferably in the range of about 10°–85° and more preferably within the range of 50°–800°; in FIG. 3, this angle is labelled θ. The four channels of collection are preferably at elevation angles a that will collect scattered light from 3°–30° from the plane of surface 40.

FIG. 5 is a schematic view of three positions of the illuminated area on a surface to be inspected to illustrate the scanning and data gathering process of system 20. As shown in FIG. 5, at one instant in time, beam 38 illuminates an area 10 on surface 40. Area or spot 10 is divided into sixteen pixels by grid lines x1–x5, y1–y5. In this context, the term "pixel" is meaningful only in reference to the taking of data samples across the intensity distribution such as that in FIG. 1B and subsequent data processing and is borrowed from data sampling and processing in other technologies such as video technology. The pixel that is bounded by grid lines x2, x3 and y2, y3 is pixel P shown as a shaded area in FIG. 5. If there is an anomaly in this pixel P, and if the light illuminating pixel P has the intensity distribution as shown in FIG. 1B with a high intensity level between grid lines y2 and y3, light scattered by the anomaly will also have a high intensity. However, as the beam moves along the Y axis so that the area 10' is illuminated instead, pixel P will still be illuminated but at the lower intensity level of that between grid lines y1 and y2; in reference to FIG. 1B, the intensity of the illumination is that between grid lines y1 and y2 in FIG. 1B. Therefore, if the sampling rate employed by the data processor 130 in FIG. 3 for processing light detected by the collection or collector channels 110a, 110b, 111a, 111b is such that a sample is taken when the illuminating beam is in position 10 and when the illuminating beam is in position 10', then two data points will be recorded. Thus for any pixel such as P, a number of data points will be taken, one when the illumination is at a higher level as illustrated by data point D2 in FIG. 1B and another one when the illumination is at a lower level, illustrated at data point D1 in FIG. 1B. If position 10 is not the starting position of the sweep 50 illustrated in FIGS. 3 and 4, then two prior samples would have been taken prior to the time when the illuminating beam illuminates the surface 40 in position 10, so that the processor would have obtained two more data points D3, D4 corresponding to the prior positions of the illuminating beam when light of intensity values between grid lines y3, y4 and between y4, y5 respectively illuminates such pixel P (grid lines y1 through y5 would, of course, move with the location of the spot). In other words, four separate data points D1–D4 would have been taken of the light scattered by an anomaly present in pixel P as the illumination beam illuminates pixel P when scanning along the Y direction.

In most laser beams, the beam intensity has a Gaussian intensity distribution not only in the Y direction but also in the X direction. For this reason, after the illuminating beam completes the scanning operation for scanning a sweep such as sweep 50 as shown in FIG. 4, and when the illuminating beam returns to position 74 for scanning the adjacent sweep 50', it is desirable for the illuminated area along sweep 50' to overlap that of sweep 50 so that multiple samples or data points can again be taken also along the X direction as well as along the Y direction. Spot 10 is not drawn to scale in FIG. 4 to show overlap between adjacent sweeps. Therefore, when the illumination beam is scanning along sweep 50' from starting position 74 as shown in FIG. 4, the area illuminated would overlap spot 10; this overlapping spot is 10" as shown in FIG. 5, where the spot 10" is displaced along the negative X direction relative to spot 10 by one quarter of the long axis of the ellipse 10 and 10".

Point Spread Function

The Gaussian intensity distribution illustrated in FIG. 1B is known as the point spread function of the combined illumination and light collection system 20 of FIG. 2. As discussed above in reference to FIGS. 1B, 5 above, the point spread function is a function of both x and y pixel positions. In FIG. 2, the illumination system illuminates a small area of the surface 40 and the intensity distribution of such illumination essentially determines the point spread function of system 20.

Alternatively, in imaging type systems, such as those described in U.S. Pat. Nos. 4,532,650; 4,579,455; 4,805,123; and 4,926,489 referenced above, the illumination system illuminates a large area of the surface, the light from the surface to be inspected is focused by a light collection system in a manner similar to that of a camera. In such imaging systems, the design of the light collection system determines the point spread function of the combined illumination and light collection system. The point spread functions of most such imaging systems also have Gaussian distributions of the form shown in FIG. 1B, and the above description concerning scanning and data acquisition can be generally applied to these imaging systems. Therefore, in both types of systems, when the intensity of the detected light is sampled, and when such sampled data is used for the detection and verification of anomalies, the characteristics of such point spread functions are taken into account as described in detail below. In other words, the data processing scheme described below, including the detection and verification processes, is applicable to both types of systems.

Terminology and Setting for Data Processing

Anomalies are identified by comparing intensity levels or values from corresponding pixel locations of images of adjacent instances of a repeating pattern—referred to as a strip unit (described below in detail)—on the wafer surface, where the repeating pattern may be a real one such as that of memory or logic devices on a semiconductor wafer. In the case of a non-patterned wafer, it is sometimes useful to define an imaginary repeating pattern; both types of patterns are referred to herein as repeating patterns, and strip units can be defined with respect to such repeating patterns. Scattered light images from corresponding locations of adjacent strip units are buffered and compared, where the image in which anomalies are being sought is referred to as the target image and the other image (against which it is compared) is referred to as the reference image.

The data processing portion of the system of this invention employs pixels of the order of several microns in size, which is considerably larger than the submicron pixel size of the imaging type systems described above. Furthermore, in the preferred embodiment, by monitoring variations in the height of the surface to be inspected and correcting for such variations using an automatic positioning system and other measures as explained below, it is possible to achieve local data registration of better than ±1 pixel in accuracy. These factors are exploited in the data processing design to enable less expensive and more efficient detection and verification of anomalies.

FIG. 6 is a schematic diagram of a semiconductor wafer to illustrate the invention. The axes $X_w$ and $Y_w$ axes define the wafer coordinate system and the $X_s$ and $Y_s$ axes define the stage coordinate system. In general, the width of any region on the wafer is measured along the X direction and the height of any region on the wafer is measured along the Y direction. During the above-described wafer scanning process, the X-stage axis is defined as the scan axis (mechanical scan direction) and the Y-stage axis is defined as the step axis. As described above, the illumination system scans linearly and uni-directionally along the sweep axis, which is parallel to the Y axis. Also as described above, the illumination system scans strips such as 54 and 56 in a serpentine pattern of strips as also illustrated in FIG. 6. In general, a strip scan denotes the scan of a single strip, and a scan refers generically to the acquisition of data from a wafer region, regardless of its size.

This invention employs strip-unit-to-strip-unit comparison (defined below) which assumes that the pattern on the wafer repeats in a periodic fashion as shown in FIG. 7. The fundamental repeating pattern unit on the wafer is a die and the two-dimensional spatial layout of die is called a die grid. In some instances, the fundamental repeating pattern may actually be a stepper field comprised of several die.

The data processing portion of the system is defined relative to the current strip scan (as shown in FIG. 8). The data processing coordinate system is defined by the scan and sweep axes defined above and has units of sweeps of the scan axis and units of pixels along the sweep axis. The sweep number monotonically increases across the strip scan, regardless of the direction of the X-stage motion during the scan. The fundamental repeating pattern unit along a strip scan is denoted a strip unit. The height of a strip unit (which is equal to the height of the strip scan) is defined as the height (length) of a sweep and the width of a strip unit is defined as the width of a die. A strip unit may be comprised of several die and/or die segments as shown in FIG. 9, where a die segment is a portion of a die contained within a strip unit. Therefore, the height of a strip unit may contain exactly one die, a segment of a die, segments of two die, several whole die, or several whole die bounded by segments of one or two die. In the case of a non-patterned wafer, it is sometimes useful to define a virtual die and a corresponding virtual die grid, so that the definition of the strip unit above applies to non-patterned wafers as well.

It is preferable for the illumination beam to be aligned with the real or virtual patterns on the surface inspected (e.g. with the "streets" between die patterns), so that the intensity values obtained by the light collection subsystem from adjacent patterns can be used for indicating anomalies. Such alignment is known to those skilled in the art and is discussed, for example, in Stonestrom et. al, referenced above.

Data Processing Subsystem

FIG. 10 is a functional block diagram of the data processing subsystem 130 to illustrate the invention. During the scan of a surface, sweep generation by chirp generator 80 and data acquisition in the manner described above in reference to FIGS. 1A–5 are synchronized with data processing by timing signals that are generated by timing electronics 84. The timing signals from board 84 are, in turn, synchronized to the X-stage encoder 135. Therefore, as the illuminating beam sweeps the wafer surface, the collected light signal is digitized by the analog board 134 and passed to the data processing board 136 for processing. In order to process the collected light signal from four collection channels independently, each channel has its own analog board and data processing board, where all channels derive their timing information from a common timing electronics board 84. The timing electronics board 84 controls, among other functions, the intersweep distance, strip-unit width, and the number of strip units that will be acquired.

Data Processing Board 136

FIG. 11 is a block diagram showing in more detail the data processing board 136 of FIG. 10. Analog board 134 converts the intensity data from one of the collectors 110a, 110b, 111a, 111b to digitized data. The incoming digitized data from the analog board is first stored in a data buffer 142 of a memory management unit 140 after a certain delay by delay element 144. The delay is to allow time for the board 136 to process the data stored in the buffer 142 before it is over-written by new incoming data. Memory management unit 140 supplies the buffered and incoming data to four parallel paths: two detection stages 152, 154 and two verification stages 162, 164. The reason for having simultaneous processing by two different detection stages and two different verification stages is explained below. FIG. 12 is a schematic diagram illustrating the strip inspection mode in which data from strip units are compared for detection and verification of anomalies.

In the preferred embodiment, the detection and verification stages are stream-based processing stages that process data at a rate substantially equal to the average sampling rate of the system. The sampling rate is in turn synchronized with the scan rate of the surface as noted above. Also preferably, the detection and verification stages process the incoming data simultaneously; it being understood that it is possible for the detection and verification stages to be applied sequentially instead, all such variations being within the scope of the invention.

In reference to FIGS. 11, 12, the intensity data acquired for strip unit N–1 is compared to the intensity data acquired during a number of previous sweeps for the strip unit N–2 and is also compared to the intensity data that will be acquired and forthcoming from memory management unit 140 for the strip unit N. In such comparison, the intensity data for the strip units N–2 and N are taken as the reference images for comparison with the target image in strip unit N–1. Where strip unit N is the target image, then units N–1 and N+1 are the respective reference images for comparison. Therefore, for each pair of strip units N–1, N, two comparisons are performed: one where N–1 is the target image and N is the reference image, and the other where N is the target image and N–1 is the reference image. For this reason, it would be advantageous and more efficient to perform both comparisons simultaneously. After further processing by anomaly detection logic 172, 174 and the event processing stage 180, the results of the comparisons are supplied to the system Central Processing Unit (CPU) 131 of FIG. 10 to be combined with other comparisons for anomaly detection and verification. For example, the further processed result of the comparison where N is the target image and N–1 is the reference image is supplied to the system CPU. At a later point in time, the intensity data for the strip unit N+1 is acquired and received by board 136 and is then used as a reference image to be compared to the target image in strip unit N. The further processed result of such comparison is also supplied to the system CPU to be combined with the result of comparison where N is the target image and N–1 is the reference image for anomaly detection and verification.

The outputs of the detection and verification stages 152, 162 are supplied to anomaly detection logic 172 for determining the presence of anomalies in strip unit N. In the same vein, detection and verification stages 154, 164 supply their outputs to anomaly detection logic 174 for determining the presence of anomalies in strip unit (N–1). The outputs of the detection logic 172, 174 are then processed by an event processing stage 180 which detects and characterizes events, where an event is defined as a connected region of (verified) anomalous pixels. The event processing stage 180 buffers events data and signals the availability of event data to the system CPU 101 through a download FIFO 182.

Strip Inspection Mode

Strip Inspection (the inspection of a strip) is the principal mode of operation of the data processing board. The detection stage preferably detects anomalous pixels using strip-unit-to-strip-unit comparison. In the preferred embodiment, a pixel is considered anomalous if the difference between its intensity value and that of the corresponding pixel in the neighboring strip unit exceeds the expected variation due to system errors. A verification stage verifies the anomalous pixels in order to remove false-positives. In the preferred embodiment, the verification stage processes the incoming data in parallel with the detection stage.

In reference to FIG. 11, the purpose of the event processing stage is to assemble and characterize events, where an event is defined as a connected region of verified anomalous pixels. An event is characterized by its location, extent, integrated intensity difference, and integrated reference intensity. The event processing stage buffers event data and signals the availability of event data to the system central processing unit.

A Post-Processing Stage (not shown) is preferably used as follows. The purpose of the Post-Processing Stage is to upload the event data from the Data Processing Board and merge event data on a wafer-scale basis. The responsibilities of the Post-Processing Stage generally include the following: (1) merging events (events that either: (a) were truncated in width along the strip or (b) intersected with the upper or lower boundary of the strip); (2) converting event locations to wafer coordinates; (3) applying calibration corrections to event coordinates; (4) merging event data from multiple channels; (5) classifying events by size (using event intensity information); and, (6) generating an event file.

It should be noted that although the Strip Inspection mode of operation may be executed repeatedly, in the preferred embodiment, the Data Processing Board 136 has no knowledge of prior executions. For example, performing a full-wafer inspection requires numerous executions of the Strip Inspection mode of operation—one for each strip. Given this "strip-oriented" nature of the Data Processing Board, it is the responsibility of the controlling software on the System CPU to request each of these strip scans and then merge the results.

Detection and Verification Stages

In reference to FIG. 11, since the two pairs of stages 152, 162 and 154, 164 process two sets of strip unit images simultaneously (strip unit N as the target image as compared against strip unit N−1 as the reference image and vice versa), the processing is identical in the two pairs of stages. Therefore, the detection and verification processes that take place in both pairs of stages will be described by reference to a single set of target and reference images.

In the preferred embodiment of the detection and verification processes, it is assumed that the pixels of the target strip-unit image are registered to an accuracy of within ±1 pixel in any direction with the corresponding pixels of the reference strip-unit image to which they are compared. This is achieved by means of precise system design and scan synchronization as described above and by a positioning system described below, which is the subject of parent application "Optical Wafer Positioning System," by Mehrdad Nikoonahad, Philip R. Rigg, Keith B. Wells, and David S. Calhoun, Ser. No. 08/361,131 filed Dec. 21, 1994. The net result is that the misregistration is within the range of ±1 pixels in any direction.

In the preferred embodiment, four samples are taken of the illuminating spot where the illumination intensity exceeds $1/e^2$ of the peak intensity, or equivalently, at the rate of four samples per $1/e^2$ width of the point spread function. It is of course possible to acquire more samples of the illuminating spot, although as will be obvious from the description above in reference to FIG. 5, more samples taken means that more time will be required to acquire the data samples at the expense of reduced throughput. The detection and verification processes described herein can evidently be altered where more or fewer than four samples are taken of the illuminating spot. In the preferred embodiment, it is also assumed that anomalies are bright relative to the "underlying" pattern; however, if certain surface or near surface defects appear as dark areas relative to the "underlying" pattern, it will be evident to those skilled in the art that all one needs to do is to invert the intensity values that are employed in the detection and verification processes described below for detecting such dark defects. While the interaction of the illuminating light with anomalies and patterns can be complicated, as a practical matter, the pattern and anomaly signals "superpose" or simply add in many instances and this fact can be taken advantage of in the detection and verification scheme described below.

The operation of the detection stage will now be described in reference to FIG. 13 which is a block diagram of the detection stage of FIG. 11. In reference to FIGS. 11 and 13, the intensity value data for strip unit N−1 stored in data buffer 142 in FIG. 11 is supplied as an input to the detection and verification stages 152, 154, 162, 164 and the intensity data of the incoming data stream to board 136 for strip-unit N is the other input to these stages. Such incoming data is sent from analog board 134, which receives the data from one of the four detectors 110a, 110b, 111a, 111b of FIG. 3.

Each of the N−1 and N strip units includes a number of intensity values, each for a particular pixel location within the strip unit. Typically, a strip unit would include pixel data from scanning a number of adjacent sweeps such as 50, 50', etc., in FIG. 4. The intensity of the pixel at pixel location (x, y) of the target image (strip unit N) is $I_T(x, y)$ and the intensity value for the same pixel location in the reference image (strip unit N−1) is $I_R(x, y)$. Pixel location (x, y) has eight neighbors: (x−1, y−1), (x, y−1), (x+1, y−1), (x−1, y), (x+1, y), (x−1, y+1), (x, y+1), and (x+1, y+1); together with (x, y), they form a 3×3 matrix of pixel locations centered at pixel location (x, y). The intensity values at these pixel locations form a three by three matrix of intensity values: [$I_T(x−1, y−1)$, $I_T(x, y−1)$, $I_T(x+1, y−1)$, $I_T(x−1, y)$, $I_T(x, y)$, $I_T(x+1, y)$, $I_T(x−1, y+1)$, $I_T(x, y+1)$, $I_T(x+1, y+1)$]. Similarly the intensity values at the corresponding pixel locations in the reference image, strip unit N−1, also form a three by three matrix of intensity values: [$I_R(x−1, y−1)$, $I_R(x, y−1)$, $I_R(x+1, y−1)$, $I_R(x−1, y)$, $I_R(x, y)$, $I_R(x+1, y)$, $I_R(x−1, y+1)$, $I_R(x, y+1)$, $I_R(x+1, y+1)$].

In the preferred embodiment, each of these two sets of nine values is averaged by a 3×3 averaging digital filter (202, 204) to arrive at an averaged intensity value ($I_T(x, y)$, $I_R(x, y)$). These two values are then compared in a number of ways to ascertain whether an anomaly is present at such pixel location (x, y) in the target image.

In one comparison, an error threshold is preferably first derived from the difference between the averaged intensity value $I_R(x, y)$ at the output of filter 202 and the maximum of the nine averaged intensity values at the 3×3 or nine pixel locations centered at the pixel location (x, y). Thus circuit 206 determines the maximum value of the nine averaged intensity values at the nine pixels centered at (x, y) and provides an output to a subtractor 208. Subtractor subtracts the averaged intensity value $I_R(x, y)$ from such maximum value from circuit 206 and provides this difference value to a multiplier 210. If the reference image and the target image are misregistered by ±1 pixel in any direction, then this maximum value is an error potentially introduced by the system. Multiplier 210 multiplies such difference intensity value by a factor ALPHA and provides its output as an error threshold for comparison purposes.

The two averaged intensity values $I_T(x, y)$ at the output of filter 204 and the average value $I_R(x, y)$ at the output of filter 202 are subtracted by subtractor 212 and the difference value provided to three comparators 222, 224 and 226. Comparator 222 compares such difference to the expected error threshold (calculated as described above based on the maximum registration error) at the output of multiplier 210. If such difference is smaller than the error threshold, then no anomaly is detected at the pixel location (x, y) and comparator would provide an output of 0. However, if such difference of intensity values at the pixel location between the reference and target images exceeds such error threshold, then an anomaly is indicated at the pixel location (x, y) and comparator 222 would output a 1.

In the above description, it is indicated that by means of a positioning system and other measures, misregistration error is expected to be ±1 pixel location. Even if the error turns out to be less than or more than ±1 pixel location, (e.g. between 0 and ±2 pixel locations), an error threshold can still be calculated based on interpolation; in such event ALPHA is set to a multiple of the maximum intensity difference derived as described above, where the multiple is a positive number, such as one ranging from 0 to 2. This interpolation process exploits the smooth shape of the point spread functions of most combined illumination and light collection systems.

In the above comparison, the average intensity values of a 3×3 matrix of pixel locations with (x, y) at the center of the matrix is used for both the target and reference images. The size of the matrices is chosen to cover substantially the point spread function of the combined illumination and light collection system, with pixel location (x, y) at or near the peak of the function. Thus in reference to FIG. 1B, 5, for example, it will be seen that a 3 pixel by 3 pixel matrix around the target pixel location being processed, such as pixel P, will cover substantially the point spread function of the system. If pixel P is actually at the center of spot 10 instead of being slightly off to the side towards the left and downwards, then the 3 by 3 matrix will actually cover the top portion of the function as will be seen from FIG. 1B.

In some circumstances, the difference of intensity values between the target and reference images (based on maximum misregistration error) can exceed the expected threshold if the intensity values compared contain significant noise not accounted for by the expected error threshold at the output of multiplier 210. In such event, the above-described process can yield a false-positive which can be reduced by comparing the intensity difference value at the output of subtractor 212 to an absolute minimum error threshold ABSMIN by means of comparator 226, where ABSMIN is a function of system noise (i.e. noise inherent in the method). As in the case of comparator 222, if such intensity difference value between the reference and target is less than ABSMIN, no anomaly is indicated and comparator 226 would output a 0. Otherwise, a possible anomaly is indicated and comparator 222 would output a 1.

Furthermore, some system error can be expected on account of the sampling process itself which is essentially an analog-to-digital conversion process. In reference to FIG. 1B, it will be seen that depending on the location of the point spread function at which data samples are taken, a difference between the intensity values of the target and reference images at corresponding pixel locations can be caused by such sampling process rather by the presence of any anomaly. In view of the Gaussian shape of the point spread functions of most combined illumination and light collection systems, such system error can be accounted for by computing an error threshold equal to a percentage (e.g. 12%) of the averaged reference intensity value at the pixel location. Thus multiplier 230 multiplies the output of filter 202 by a percentage factor PRCNT and provides the product as an error threshold to comparator 224 which compares the intensity difference value at the output of subtractor 212 to such threshold. If the difference value is less than the threshold, no anomaly is indicated and comparator 224 would output a 0; otherwise, a possible anomaly is indicated and comparator 224 outputs a 1 instead.

The outputs of all three comparators 222–226 are combined by anomaly detection logic to determine whether an anomaly is present at the pixel location (x, y). The same process is then performed for all other pixel locations within the target image, that is, the strip unit N. For pixel locations at the perimeter of the strip unit, the above process is not performed and their values can be simply set to 0. While in the preferred embodiment, the outputs of all three comparators 222, 224 and 226 are used for determining the presence of anomalies, it will be understood that comparators 224 and 226 for reduction of the rate of false-positives are not essential and can be omitted in some applications.

The relatively smooth Gaussian distribution of the point spread functions of many combined illumination and collection systems can be exploited to enhance anomaly detection. If an anomaly is present in the target image but not in the reference image, one would expect that the intensity values at at least some of the 3×3 matrix of pixel locations in the target image will be greater than those at the corresponding pixel locations in the reference image. This is referred to herein as the Neighbor Restriction Criterion, the term indicating that one would expect the intensity value of each of some if not all of the nine target pixel locations to be greater than the intensity value at the corresponding pixel location of the 3×3 matrix in the reference image. This is performed by the Neighborhood Restriction Criterion circuit 232.

In the preferred embodiment, circuit 232 provides a 1 indicating the presence of an anomaly in the target image if the intensity value of each of the nine pixel locations of the target image is greater than the intensity value of the corresponding location of the nine pixel locations in the reference image, where the pixel location (x, y) is at the center of both matrices. Otherwise, circuit 232 provides a 0 to the anomaly detection logic 240.

In some applications, it may be useful to relax the Neighbor Restriction Criterion so that circuit 232 determines whether, for each of at least some but not all nine of the pixel locations, the intensity value at each pixel location of the target image is greater than the intensity value of the corresponding pixel location in the reference image. Such and other variations are within the scope of the invention.

On some surfaces to be inspected, the high intensity of light scattered from the surfaces themselves renders the use of the error thresholds ABSMIN, PRCNT ineffective. In such event, it is preferable to employ other thresholds instead.

Comparator 234 compares the averaged intensity value $I_T(x, y)$ at the output of filter 204 to a saturation threshold SATTHRESH, and if the intensity value exceeds such threshold, an anomaly is indicated and comparator 234 would output a 1; otherwise, it would output a 0 indicating the absence of anomalies. If the averaged intensity value $I_R(x, y)$ in the reference image is also smaller than a threshold MAXREFATSAT (indicating the maximum reference intensity value at which the criterion is applied), while the average value for the target image exceeds the saturation threshold, then an anomaly is indicated. This is performed by comparator 236 which compares the averaged intensity value $I_R(x, y)$ to MAXREFATSAT, and outputs a 1 if the intensity value is lower than the threshold and a 0 if the intensity value exceeds the threshold to logic 240. Thus in the case where the intensities in the reference and target images are both high, this may cause the averaged intensity values $I_T(x, y)$ and $I_R(x, y)$ to both exceed their respective thresholds, then no anomaly is indicated. This is desirable since the apparent anomaly is caused by the high scattering of the surface in both the reference and target images. In the preferred embodiment, a saturated anomaly is indicated at the pixel location (x, y) only when the outputs of comparators 222, 234, 236 are all 1's, or when the outputs of comparators 222, 224, 226 are all 1's and when the neighborhood restriction criterion is met. Thus in the preferred embodiment, an anomaly is indicated if the following conditions are met:

(1) The pixel location is not at the perimeter or boundary of strip unit;

(2) The outputs of comparators 222, 224, 226 are all ones or the outputs of comparators 224, 234, 236 are all ones; and (3) The output of the neighborhood restriction criteria circuit 232 is 1.

The above-described process for detection is summarized below in a mathematical description of the preferred embodiment.

Mathematical Description of Detection Stage Algorithm

Algorithm Overview (1) A 3×3 averaging operator is applied to each strip-unit image as a means of reducing the sensitivity to sampling errors.

(2) Error thresholds for each location of the target image are generated directly from the reference image by searching over the eight-connected neighborhood centered at the corresponding location in the reference image in order to determine the maximum increase in intensity that would be expected due to misregistration. Linear interpolation of threshold values is used to calculate threshold values for subpixel errors. Minimum thresholds are enforced in order to deal with local peaks, uniform regions, and low-scatter regions.

(3) A Neighborhood Restriction Criterion (NRC) is enforced, which requires each intensity value in the eight-connected (3×3) neighborhood of the target image to be greater than its corresponding value in the reference image. This exploits the expected contrast of the anomaly as well as the extent of the point spread function.

(4) A pixel is anomalous if: (a) its intensity value is larger than its corresponding reference value by an amount that exceeds the calculated thresholds; and, (b) the Neighborhood Restriction Criterion is satisfied.

(5) Explicit provision is made for the detection of saturated anomalies on top of flat, high-scatter backgrounds. Hence, a pixel is anomalous if it meets either the detection criteria described above or the Saturated-Anomaly Criterion.

Detection Stage Algorithm

The intent of this section is to mathematically describe the application of the detection algorithm to a single set of target and reference images without regard to implementation details.

Definitions

W—Image Width (pixels).

H—Image Height (pixels).

x—Horizontal coordinate; values are in the range [O, W−1].

y—Vertical coordinate; values are in the range [O, H−1].

m—Horizontal coordinate; values are in the range [O, W−1].

n—Vertical coordinate; values are in the range [O, H−1].

$I_T(x, y)$—Target Image.

$I_R(x, y)$—Reference Image.

$\overline{I_T}(x, y)$—3×3 averaged version of Target Image.

$\overline{I_R}(x, y)$—3×3 averaged version of Reference Image.

ALPHA—Multiplicative constant used for linearly interpolating error threshold due to misregistration.

ABSMIN—Absolute minimum error threshold value at any location.

PRCNT—Percentage (expressed as a decimal number) used to calculate a minimum error threshold at each location based on the reference intensity value.

ATOL(x, y)—Array of interpolated error thresholds.

PTOL(x, y)—Array of percentage increase error thresholds.

SATTHRESH—Saturated anomaly threshold—image intensity value above which a pixel is defined as saturated.

MAXREFATSAT—Maximum intensity that a saturated pixel's corresponding reference location can have in order for the saturated pixel to be considered anomalous.

NRC(x, y)—Array of Neighborhood Restriction Criterion (NRC) values.

AM(x, y)—Anomaly Map for Target Image.

Algorithm

Step #1. Apply 3×3 averaging

Generate 3×3 averaged versions of the target and reference images by running a 3×3 averaging operator across them. Perimeter pixels (for which the 3×3 average is not defined) are set to have a value of zero. In the following equations, "AVE" is an averaging operator that calculates the average of the specified values:

$$\overline{I_T}(x, y) = \frac{\begin{array}{c} AVE[I_T(x-1, y-1), I_T(x, y-1), I_T(x+1, y-1), \\ I_T(x-1, y), I_T(x, y), I_T(x+1, y), I_T(x-1, y+1), \\ I_T(x, y+1), I_T(x+1, y+1)], \\ \text{if } x \text{ is in the range } [1, W\text{-}2] \\ \text{and } y \text{ is in the range } [1, H\text{-}2] \end{array}}{0}$$

else; and $$\overline{I_R}(x, y) = \frac{\begin{array}{c} AVE[I_R(x-1, y-1), I_R(x, y-1), I_R(x+1, y-1), \\ I_R(x-1, y), I_R(x, y), I_R(x+1, y), I_R(x-1, y+1), \\ I_R(x, y+1), I_R(x+1, y+1)], \\ \text{if } x \text{ is in the range } [1, W\text{-}2] \\ \text{and } y \text{ is in the range } [1, H\text{-}2] \end{array}}{0}$$

else.

Step #2. Generate array of interpolated error thresholds based on maximum registration error Generate error threshold array from the averaged reference image. Border pixels (for which the error thresholds are not defined) are set to have a value of zero. In the following equation, "MAX" is maximum operator that calculates the maximum of the specified values:

$$ATOL(x, y) = \frac{\begin{array}{c} ALPHA*(MAX[\overline{I_R}(x-1, y-1), \overline{I_R}(x, y-1), \\ \overline{I_R}(x+1, y-1), \overline{I_R}(x-1, y), \overline{I_R}(x, y), \\ \overline{I_R}(x+1, y), \overline{I_R}(x-1, y+1), \overline{I_R}(x, y+1), \\ \overline{I_R}(x+1, y+1)] - \overline{I_R}(x, y)) \\ \text{if } x \text{ is in the range } [2, w\text{-}3] \\ \text{and } y \text{ is in the range } [2, H\text{-}3] \end{array}}{0}$$

else.

Step #3. Generate array of percentage-increase error thresholds

Generate error threshold array from the averaged reference image. Border pixels (for which the error thresholds are not defined) are set to have a value of zero.

$$PTOL(x, y) = \frac{\begin{array}{c} PRCNT*\overline{I_R}(x, y) \\ \text{if } x \text{ is in the range } [1, W\text{-}2] \\ \text{and } y \text{ is in the range } [1, H\text{-}2] \end{array}}{0}$$

else.

Step #4. Generate Neighborhood Restriction Criterion array

Generate Neighborhood Restriction Criterion array for target image. Perimeter pixels (for which the 3×3 Neighborhood Restriction Criterion is not defined) are set to have a value of zero. Note that these calculations use the original (not the averaged) image intensity values.

$$NRC(x, y) = \begin{cases} 1 \text{ (criterion satisfied)} \\ \text{if: } (i) \ x \text{ is in the range } [1, W\text{-}2]; \\ \quad (ii) \ y \text{ is in the range } [1, H\text{-}2]; \\ \quad \text{and, } (iii) \ I_T(m, n) > I_R(m, n) \text{ for} \\ \quad \text{all } m \text{ in the range } [x-1, x+1] \text{ and} \\ \quad \text{all } n \text{ in the range } [y-1, y+1] \\ \hline 0 \text{ (criterion not satisfied)} \\ \text{else} \end{cases}$$

Step #5. Generate Anomaly Map

Generate Anomaly Map. Border pixels (for which detection is not possible) are set to have a value of zero.

$$AM(x, y) = \begin{cases} 1 \text{ (anomalous)} \\ \text{if: } (i) \ x \text{ is in the range } [2, W\text{-}3]; (ii) \\ \quad y \text{ is in the range } [2, H\text{-}3]; (iii) \\ \{((I_T(x, y) - I_R(x, y)) > ATOL(x, y)) \text{ and} \\ \quad ((I_T(x, y) - I_R(x, y)) > ABSMIN) \text{ and} \\ \quad ((I_T(x, y) - I_R(x, y)) > PTOL(x, y))\} \text{ OR} \\ \{((I_T(x, y) - I_R(x, y)) > ATOL(x, y)) \text{ and} \\ \quad (I_T(x, y) > SATTHRESH) \text{ and} \\ \quad (I_R(x, y) < MAXREFATSAT)\}; \text{ and,} \\ \quad (iv)NRC(x, y) = 1. \\ \hline 0 \text{ (not anomalous)} \\ \text{else} \end{cases}$$

In the preferred embodiment of the detection stage described above, averaged intensity values for the pixel location (x, y) are used in a filtering process. In some applications, however, it may be desirable to use the intensity value at the pixel location without averaging. For this purpose, filters 202, 204 can be disabled by an appropriate input at the terminal ENABLE_AVE so that the filters would simply pass through the intensity value of the pixel location that is being processed instead of an average over a 3×3 matrix of pixel locations. Similarly, the neighborhood restriction criteria circuit 232 can also be enabled or disabled by the appropriate input at terminal ENABLE_NRC. The remaining functions of FIG. 14 can all be enabled or disabled by setting the appropriate values for the different thresholds or multipliers, such as ABSMIN, PRCNT, ALPHA, SATTHRESH, and MAXREFATSAT.

The 3×3 matrix employed in filters 202, 204 and neighborhood restriction criteria block 232 as well as maximum value circuit 206 are chosen to substantially cover the region of the point spread function with intensities above $1/e^2$ of the maximum intensity of the illuminated spot. Where more or fewer pixels or samples are taken per illuminated spot, the size of such matrices is preferably altered accordingly to again cover most of the point spread function above the $1/e^2$ intensities.

Where the target image and reference image may be misregistered by more than ±2 pixel locations, the size of the maximum value circuit 206 may need to be enlarged. Thus, where the misregistration error is ±n pixel locations, the size of the maximum value circuit 206 is preferably chosen to be 2n+1 by 2n+1. If the misregistration error is so large that there is inadequate overlap between the target and reference images, the interpolation process for setting ALPHA described above may not be applicable.

In the above description, the maximum value circuit 206 computes the difference between the maximum averaged (or unaveraged) intensity value of the nine pixels in the three by three matrix centered at location (x, y) in the reference image and the averaged (or unaveraged) intensity at the pixel location (x, y) in the reference image. It will be understood that it may also be possible to compute the value based on the maximum difference between any pair of intensity values in the 3×3 matrix. Such and other variations are within the scope of the invention.

Verification Stage

Simultaneously with or after the detection of anomalies in a strip unit N, the same reference image (strip unit N−1) and the target image (strip unit N) are provided to the verification stage 162, 164 of FIGS. 11 and 14 in order to verify that the anomalies are not false-positives. The processing in the verification stage is comprised of three comparisons.

In one comparison, it is determined whether the difference between the averaged intensity values of the target and reference images at anomalous pixel location (x, y) far exceeds a High Contrast threshold in a criterion known as the High Contrast Criterion. This is based on the notion that if the difference between the averaged intensity values of the target and reference images at such pixel location far exceeds a particular threshold (such as by a positive number multiple in the range of 2 to 16), there is no other explanation other than the presence of an anomaly. Thus similar to digital filter 202 of FIG. 13, digital filter 252 also provides an averaged value of the intensity values at the 3×3 pixel locations with the pixel location (x, y) at the center and provides it to a multiplier 256. Multiplier 256 multiplies such averaged reference intensity by a value HCCTHRESH having a value preferably in the range of 2 to 16 and provides the product to comparator 260. Digital filter 254 also performs an averaging function on the intensity values at the 3×3 pixel locations for the target image with the pixel location (x, y) at the center in a manner similar to that performed by filter 204 in FIG. 14. Such averaged intensity value for the target pixel location is then compared to the output of multiplier 256 by comparator 260. If the averaged intensity value for the target image is greater than the output of multiplier 256, comparator 260 would output a 1; otherwise, it would output a 0.

Even where the above-described High Contrast Criterion is not satisfied, an anomaly can still be indicated if the combined intensity at a number of pixel locations at and surrounding the anomalous pixel location in the target image is greater than the combined intensity values at corresponding pixel locations in the reference image by an amount that exceeds both a percentage of the combined values for the reference image and an absolute minimum threshold. This is performed by two 5×5 convolution filters or convolvers 272, 274. The two convolvers preferably use 5×5 kernel matrices of the following form:

$$\begin{bmatrix} -1/16 & -1/16 & -1/16 & -1/16 & -1/16 \\ -1/16 & 1/9 & 1/9 & 1/9 & -1/16 \\ -1/16 & 1/9 & 1/9 & 1/9 & -1/16 \\ -1/16 & 1/9 & 1/9 & 1/9 & -1/16 \\ -1/16 & -1/16 & -1/16 & -1/16 & -1/16 \end{bmatrix}$$

In reference to FIG. 1B, four data samples are taken at four pixel locations across the point spread function. The point spread function is of course a function of both variables x and y, where FIG. 1B only shows a cross-section of the function showing its dependence on the y coordinate. Therefore, if one were to provide a 3×3 matrix of intensity values to cover the point spread function, one would choose a 3×3 matrix of pixel locations with pixel location (x, y) being processed at or near the center of the matrix. This is in fact the underlying concept of choosing the 3×3 matrices for the digital filters 202, 204, 252, 254, maximum circuit 206 and Neighborhood Restriction Criterion circuit 232. If one were to include the sixteen pixel locations immediately contiguous to the nine pixel locations already chosen (the nine forming the core pixel locations), then such perimeter pixel locations would overlap the point spread function at or near areas where the values of the point spread function is $1/e^2$ of the maximum intensity of the function.

Frequently semiconductor process variations can cause the reflectivity of regions of the surface to change. By using the convolvers 272, 274 as described above, false-positives caused by such process variations can be much reduced. Since the semiconductor process variations typically cause a whole region of the surface to change its reflectivity where such regions are large in comparison with the spot size being sampled, such variations typically do not cause reflectivity changes that are local in nature. This fact can be exploited using the convolvers 272, 274. As shown in the values of the 5×5 matrix above, the matrix elements (core matrix elements) corresponding to the core pixel locations of the value 1/9, whereas the matrix values (perimeter matrix elements) corresponding to the perimeter pixel locations are −1/16. In the convolving process, each matrix element is multiplied by the intensity value of each corresponding pixel location and all twenty-five products are then summed to provide a convolved value. By convolving such matrix with a 5×5 matrix of intensity values at the 5×5 matrix of pixel locations described above, the change in reflectivity caused by semiconductor process variations would cancel out since such effect would be present at the core pixel locations as well as at the perimeter pixel locations. Since the matrix elements assigned to the core pixel locations are positive and those assigned to the perimeter pixel locations are negative, the above-described convolving process would cause such common error to be cancelled. Obviously, similar results can be achieved where the core matrix elements are negative and the perimeter matrix elements are positive (e.g. for verifying dark instead of bright defects).

Preferably, all of the core matrix elements have equal values and all of the perimeter matrix elements also have equal values. The sum of all matrix elements is preferably zero.

Under some circumstances, it may be convenient to estimate the nine values of the matrix above corresponding to the nine core pixel locations to be different from those shown above. In one embodiment, elements at the nine core pixel locations are assigned the value 1/16 instead of 1/9 and elements at the sixteen perimeter pixel locations are assigned the value −1/32 instead of −1/16.

The convolved values at the outputs of convolvers 272, 274 are subtracted by subtractor 276 to provide a difference of convolved values which is applied to comparator 280. The convolved value for the reference image provided by convolver 272 is multiplied by multiplier 278 by a factor CCPRCNT and the product is provided as a threshold to comparator 280. If the difference convolved value at the output of subtractor 276 is greater than the threshold provided by multiplier 278, a verified anomaly may be present and comparator 280 provides a 1 to logic 240; otherwise, it would provide a 0 instead. The difference convolved value at the output of subtractor 276 is also provided to comparator 282 which compares it to an absolute minimum value CCABSMIN. Thus even if the high contrast criteria is not satisfied, if both comparators 280 and 282 provide 1's to logic 240, then a verified anomaly is indicated. If either one or both of comparators 280, 282 provide a 0 to logic 240, then a verified anomaly is not present.

As in the detection stage, the size of the digital filters 252, 254 may need to be changed if more samples are taken per illuminated spot. Similarly, the size of convolvers 272, 274 may also need to be changed in such circumstances so that a single row of perimeter matrix elements of the new matrix would correspond to perimeter pixel locations substantially overlapping the $1/e^2$ points of the point spread function and the remaining core matrix elements would overlap the core pixel locations of the point spread function. The above-described process for verification is summarized below in a mathematical description of the preferred embodiment.

Mathematical Description of Verification Algorithm

Algorithm Overview (1) The High Contrast Criterion is applied at each location of the target image. For this criterion, the ratio of the 3×3 averaged target intensity to the 3×3 averaged reference intensity at each location is calculated and compared to the high contrast threshold. If the high contrast threshold is exceeded, the location is considered verified as TRUE (i.e., it is part of a true event as opposed to a false-positive). The High Contrast Criterion facilitates verification of high contrast anomalies.

(2) The Convolution Criterion is applied. For this criterion, the target and reference images are each convolved with a 5×5 convolution kernel. A threshold value for each location in the convolved target image is calculated by multiplicatively scaling the corresponding value in the convolved reference image. A minimum threshold value—which may be specified on region basis via region-based multi-based multi-thresholding—is enforced in order to deal with local peaks, uniform regions, and low-scatter regions. If the difference between the target and reference convolution values at a location exceeds the calculated threshold, the location is considered verified as TRUE. The Convolution Criterion verifies lower-contrast anomalies that cause a "significant" peak to occur in the difference between the target and reference image intensities. The Convolution Criterion also provides a key means of coping with the effects of process variations.

(3) A pixel is a verified anomalous pixel if the pixel was detected as anomalous by the Detection Stage and it meets either of the verification criteria.

Verification Stage Algorithm

The intent of this section is to mathematically describe the application of the verification algorithms without regard to implementation details.

Definitions (Note: All arrays are of size WXH except as noted.)

W—Image Wide (pixels).

H—Image Height (pixels).

x—Horizontal coordinate; values are in the range [0, W−1].

y—Vertical coordinate; values are in the range [0, H−1].

m—Horizontal coordinate; values are in the range [0, W−1].

n—Vertical coordinate; values are in the range [0, H−1].

$I_T(x, y)$—Target image.

$I_R(x, y)$—Reference Image.

$\overline{I}_T(x, y)$—3×3 averaged version of Target Image.

$\overline{I}_R(x, y)$—3×3 averaged version of Reference Image.

HCCTHRESH—High contrast threshold.

K(x, y)—Convolution kernel (5×5) for Convolution Criterion.

$CCVAL_T(x, y)$—Array of Convolution Criterion values for Target image.

CCVAL$_R$(x, y)—Array of Convolution Criterion values for Reference image.

CCABSMINS (x, y)—Array of Convolution Criterion threshold values for each location.

CCPRCNT—Percentage (expressed as a decimal number) used to calculate a Convolution Criterion threshold at each location based on its reference convolution value.

CCPTOL (x, y)—Array of percentage increase threshold values.

AM (x, y)—Anomaly Map for Target Image (from Detection Stage).

VAM (x, y)—Verified Anomaly Map for Target Image.

Algorithm

Step #1. Apply 3×3 averaging

Generate a 3×3 averaged versions of the target and reference images by running a 3×3 averaging operator across them. Perimeter pixels (for which the 3×3 average is not defined) are set to have a value of zero. In the following equations, "AVE" is an averaging operator that calculates the average of the specified values.

$$I_T(x, y) = \frac{\begin{array}{c} AVE[I_T(x-1, y-1), I_T(x, y-1), I_T(x+1, y-1), \\ I_T(x-1, y), I_T(x, y), I_T(x+1, y), I_T(x-1, y+1), \\ I_T(x, y+1), I_T(x+1, y+1)] \\ \text{if } x \text{ is in the range } [1, W\text{-}2] \\ \text{and is in the range } [1, H\text{-}2] \end{array}}{0}$$

else;

$$I_R(x, y) = \frac{\begin{array}{c} AVE[I_R(x-1, y-1), I_R(x, y-1), I_R(x+1, y-1), \\ I_R(x-1, y), I_R(x, y), I_R(x+1, y), I_R(x-1, y+1), \\ I_R(x, y+1), I_R(x+1, y+1)] \\ \text{if } x \text{ is in the range } [1, W\text{-}2] \\ \text{and is in the range } [1, H\text{-}2] \end{array}}{0}$$

else.

Step #2. Generate Convolution Criterion values

Generate convolved versions of the target and reference images by running a 5×5 convolution kernel across them. Perimeter pixels (for which the 5×5 convolution is not defined) are set to have a value of 0. Note that the following calculations use the original (not the averaged) image intensity values. Also note that the following calculation is not a "true" convolution (coordinate indices are not reversed for either the kernel or the corresponding image neighborhood); however, it becomes a true convolution if a circularly symmetric kernel is used.

$$CCVAL_T(x, y) = \frac{\begin{array}{c} \text{Sum of } K(2+m, 2+n) * I_T(x+m, y+n) \\ \text{for all } m \text{ in the range } [-2, 2] \\ \text{and all } n \text{ in the range } [-2, 2] \\ \text{if } x \text{ is in the range } [2, W\text{-}3] \\ \text{and } y \text{ is in the range } [2, H\text{-}3] \end{array}}{0.0}$$

else $$CCVAL_R(x, y) = \frac{\begin{array}{c} \text{Sum of } K(2+m, 2+n) * I_R(x+m, y+n) \\ \text{for all } m \text{ in the range } [-2, 2] \\ \text{and all } n \text{ in the range } [-2, 2] \\ \text{if } x \text{ is in the range } [2, W\text{-}3] \\ \text{and } y \text{ is in the range } [2, H\text{-}3] \end{array}}{0.0}$$

else

Step #3. Generate array of percentage-increase thresholds

Generate threshold array from the Convolution Criterion values for the reference image. Border pixels (for which the thresholds are not defined) are set to have a value of zero.

$$CCPTOL(x, y) = \frac{\begin{array}{c} CCPRCNT * CCVAL_R(x, y) \\ \text{if: } (i)) \text{ is in in the range } [2, W\text{-}3]; \\ (ii) \ y \text{ is in the range } [2, H\text{-}3] \\ \text{and, } (iii) \ CCVAL_R(x, y) > 0 \end{array}}{0}$$

else

Step #4. Generate Verified Anomaly Map

Generate Verified Anomaly Map. Border pixels (for which detection and verification are not possible) are set to have a value of zero.

$$VAM(x, y) = \frac{\begin{array}{c} 1 \text{ (anomalous)} \\ \text{if: } (i) \ x \text{ is in the range } [2, W\text{-}3]; \\ (ii) \ y \text{ is in the range } [2, H\text{-}3]; \\ (iii) \ AM(x, y) = 1; \text{ and, } (iv)\{I_T(x, \\ y) > (HCCTHRESH*I_R(x, y))\} \text{ OR} \\ \{((CCVAL_T(x, y) - CCVAL_R(x, y)) > \\ CCABSMIN(x, y)) \text{ and } ((CCVAL_T(x, y) - \\ CCVAL_R(x, y)) > CCPTOL(x, y))\}. \end{array}}{0 \text{ (not anomalous)}}$$

else

Dark Anomaly Detection

As mentioned above, in the preferred embodiment it is assumed that anomalies are bright relative to the "underlying" pattern; that is, the anomalies to be detected scatter more light than the "underlying" pattern. However, as also mentioned above, if certain anomalies are dark relative to the "underlying" pattern—that is, the anomalies scatter less light than the "underlying" pattern—then it will be evident to those skilled in the art that all one needs to do in order to detect such dark anomalies is to invert the intensity values that are processed by the detection and verification processes described above. Alternatively, it will be evident to those skilled in the art that the detection and verification processes described above can be altered to perform dark anomaly detection. In the detection process, for example, the maximum value circuit 206 would become a minimum value circuit, the neighborhood restriction criterion block 232 would require the target intensities to be less than the corresponding reference intensities, the parameters PRCNT and ABSMIN would have negative values, and the decision of each comparator 222, 224, and 226 would be reversed (that is, the comparator output equal to a 1 if A>B; 0 else). The comparators 234 and 236 would not be used. Analogous changes would be made for the verification process. Finally, it is understood that it is possible to combine instances of these altered detection and verification processes with instances of the preferred detection and verification processes, hence allowing both bright and dark anomaly detection, all such variations being within the scope of the invention.

Positioning System

The above description refers to an inspection system whereby the vertical position (height) of the surface inspected can be measured and corrected dynamically so as to reduce misregistration errors between adjacent strip units that are inspected sequentially and compared for anomaly detection. The description below entitled 37 POSITIONING SYSTEM" is taken essentially from parent application "Optical Wafer Positioning System," by Mehrdad Nikoonahad, Philip R. Rigg, Keith B. Wells, and David S. Calhoun, Ser. No. 08/361,131 filed Dec. 21, 1994.

During the scanning of the beam 38 in FIG. 2, scattered light away from the specular reflection direction is collected by detectors for detecting anomalies as described. The specular reflection of beam 38 can be advantageously used for dynamically correcting the height of the surface inspected so as to reduce misregistration errors.

The construction of APS optics 90 of FIG. 2 is illustrated in more detail in FIG. 15. FIG. 15 shows a wafer 320 having a surface 40 with an obliquely incident beam of light 38 being focused to a spot 328 on the surface 40. The incident beam 38, which may be produced by a laser, is centered about an axis 330 that is preferably in a range of between 55° and 85° from normal to the wafer surface. The incident beam 38 is primarily reflected from the spot 328 as a reflected beam 333 centered about an axis 335 oriented generally at an equal and opposite angle from normal to the wafer surface as the incident beam axis 330. While searching for anomalies on the surface 40, the incident beam 38 repeatedly scans portions of the surface, such as sweep (a), which represents one such sweep, a center of which coincides with spot 328. Sweep (a) may have a length of about 2 mm to about 10 mm in length.

The reflected beam 333 diverges from a focused "waist" at the spot 328 that may range from 5 µm to 15 µm. The divergence of the reflected beam 333 may be due to both a defocusing of the incident beam 38 beyond the waist and due to some roughness of the surface 40 that causes imperfect reflection. A telescope is placed in the path of the reflected beam 333 to image the waist of the reflected beam 333 onto a position sensitive detector 338, located near an image plane of the spot 328 and sweep (a). The telescope includes a pair of focusing lenses 339 and 340, and a spatial filter 341. The telescope may have unity magnification, or a higher magnification in order to increase the sensitivity of the detector to measuring variations in wafer height, discussed more fully below. The spatial filter 341 is positioned at the Fourier transform plane of the system, to remove higher order diffraction patterns generally caused by a patterned surface 40, while allowing specularly reflected or zero order diffracted light to pass through essentially unperturbed.

The lens 340 focuses the parallel rays of the beam 333 that pass through the spatial filter 341 onto the position sensitive detector 338 located a distance f on the opposite side of the second lens 340 from the filter 341. Thus, an image (a') of the sweep (a) is present on the detector 338.

The position sensitive detector 338 is positioned in the image plane, parallel to the Z' axis, which forms an angle φ with respect to the optical axis, defined by lens 340. Angle φ is generally in the range of 50° to 350° and is dependent upon the angle of incidence of the beam 38, with respect to the wafer surface, so that angle φ and the angle of incidence are complementary, i.e., the sum of these two angles is 90 degrees. At the spatial filter 341, the beam is stationary and only swings around a pivot point 342. As the wafer 320 moves along in the Z direction, the image of the spot 328 moves correspondingly in the Z' direction on the position sensitive detector 338.

Referring also to FIG. 15, the Z'-to-Z correspondence is dependent upon the magnification provided by lenses 339 and 340 and defined as follows:

$$\Delta Z' = -2M^2 \Delta Z_w$$

where $\Delta Z_w$ is the change in position of the wafer surface 22 along the Z axis, $\Delta Z'$ is the change in position of a corresponding image position on detector 338 and M is the magnification. A two-to-one correspondence may be obtained using unity magnification so that a one micron shift in the height of the wafer in a Z direction results in a two micron shift in the image position on the position sensitive detector in the opposite Z direction. For example, when the surface 40 is at nominal position A in FIG. 16, an image of the waist of the beam 333a reflected along sweep (a) is shown as sweep (a') on the position sensitive detector 338. Sweep (b) is shown on the surface 40 when the wafer height has moved to a lower Z height B, with respect to the nominal position A of the surface 40. As a result, a reflected beam 333b diverges and the image, (b'), of the waist of the beam reflected along sweep (b) is positioned on the position sensitive detector 338, above image (a') of sweep (a). If the wafer moves to a higher Z position C with respect to the nominal position A, a converging reflected beam 333c has its waist images on the detector below image (a') in FIG. 15, as (c') not shown in FIG. 15. A more sensitive Z'-to-Z correspondence may be obtained using higher magnification. If lenses 339 and 340 provided 2× magnification, a one micron shift in the surface height along the Z direction would correspond to an 8 micron shift on the detector along the Z' axis, in the opposite direction.

The position sensitive detector is a silicon device. It is doped with a graded concentration of dopants so that the signals out of each lead 343 and 344 is proportional to both the position and the intensity of the image on the detector 338. A mechanical window 45 is placed in the path of the reflected beam between the surface 22 and the detector 338. The mechanical window 45 defines an aperture 346, resulting in only the central portion of the light of the image of a sweep impinging on the detector 338. In response to that portion of the light impinging upon the detector 338, an electrical signal is transmitted, having a width equal to the length of time required for the image line to travel the width of the aperture 346. The width of the aperture 346, along the direction of sweep (a') and perpendicular to both the X' and Z' directions, is of sufficient size so as to create a train of signals on leads 343 and 344, synchronized with the sweep frequency.

Processing circuitry 92 receives these signals and determines the actual height of the wafer as a result of image position, without regard for the intensity of the beam impinging on the detector 338. Synchronizing the signals with the sweep frequency increases the accuracy of the height measurement by attenuating unwanted signals that may result, for example, from thermal drifts in either the electronic circuitry or optical components and ambient light. The processing circuitry 92 produces a normalized signal that may be transmitted along lead line 347 to an open loop response, e.g., to obtain a visual map of the surface 320 height variation. Alternatively, a normalized signal may be sent along lead 348 to a piezo-stage 349 that will position the wafer 320 in the Z direction so that the surface 40 is in a preferred position.

Other types of position sensitive detectors may alternatively be employed. For example, although not necessary for merely determining wafer height, a bi-directional detector may be employed to detect surface tilt along a sweep, as well as surface height. This detector would have dopants graded in a direction perpendicular to the Z' direction and would include two additional leads 346 and 347. Similar to the signals sent on leads 343 and 344, the signals on leads 346 and 347 would be proportional to both the image position and intensity. The signals on leads 346 and 347, however, correspond to the spot 328 position along a sweep (a), whereas the signals on leads 343 and 344 corresponds to the wafer height. By comparing these signals, the variation of the surface height can be determined along the sweep, thereby providing information concerning the tilt of the wafer surface.

Referring to both FIGS. 4 and 15, the reflected image of a sweep such as 50 is received by the position detector 338, which sends an electrical signal to the signal processing circuitry 92. The processing circuitry 92 causes the stage 349 to raise or lower the wafer surface 40 for a subsequent sweep 50'. In addition, if a bi-directional position sensitive detector were employed, processing circuitry 92 could cause stage 349 to rotate in order to compensate for any tilt measured in the surface 40 along sweep 50. Thus, the system of FIGS. 4 and 15 automatically positions a wafer surface 40 at a preferred height while the surface 40 is being scanned.

FIG. 17 offers an expanded view of the electronics involved in the processing circuitry 92. In the preferred embodiment, current signals are present on each of the leads 343 and 344. Each current signal represents uncorrected position information of the image on the detector 338 and can be described as follows:

$$S_1(t) = PR(t)R_\lambda G(0.5 + Z_s/D_{PSD}) \quad (1)$$

$$S_2(t) = PR(t)R_\lambda G(0.5 - Z_s/D_{PSD}) \quad (2)$$

where P is the incident power on the wafer in watts, R(t) is the reflectivity as a function of time as the sweep in a strip is scanned, $R_\lambda$ is the responsivity of the sensor in Amperes/watt, G is the gain of the transimpedance amplifier in Ohms, $z_s$ is the distance on the sensor measured in microns from a nominal position, and $D_{PSD}$ is the length of the position sensitive detector. The nominal position is a position of the reflection of the beam 38 when the surface 40 is at the desired height or position.

Each lead 343 and 344 is connected to a transimpedance amplifier 410 and 411, each of which converts the respective current signal into a voltage signal. The output of each transimpedance amplifier 410 and 411 is electrically coupled to a difference amplifier 412 and a summing amplifier 413. The difference amplifier obtains the difference between the voltage signal received from transimpedance amplifier 410 and the voltage signal received from transimpedance amplifier 411, forming a difference signal. The summing amplifier 413 adds the voltage signal received from transimpedance amplifier 410 with the voltage signal received from transimpedance amplifier 411, forming a summed signal.

The output of the difference amplifier 412 is electrically coupled to a first band pass filter 414, and the output of the summing amplifier 413 is electrically coupled to a second band pass filter 415. The first and second band pass filters 414 and 415 remove unwanted noise from the summed and difference signals by attenuating signals not having a frequency that corresponds to a range of predetermined frequencies, centered about the sweep frequency. In the preferred embodiment, filters 414 and 415 pass a 100 kHz bandwidth. Electrically coupled to receive the output of the first band pass filter 114 is a first multiplying circuit 416, and electrically coupled to the second band pass filter 415 is a second multiplying circuit 417.

The circuits 416 and 417 multiply the signals received from the band pass filters 414 and 415 by a square wave clock signal, derived from the sweep generator, and operate so as to down-convert to baseband the signals from both band pass filters 414 and 415, which are at the sweep frequency, and harmonics. This facilitate removing unwanted signals corresponding to thermal drifts and ambient light. In order to select only the baseband signals from the outputs of the multiplying circuits 416 and 417, these circuits are each electrically coupled to a first and second low pass filter 418 and 419, respectively. The first and second low pass filters have narrow bandwidths of only a few Hz. The narrow bandwidth results in the outputs of filters 418 and 419 having signals originating from a few Hz on either side of the fundamental and harmonics of the scan frequency, with all other frequencies being attenuated. Both the first and the second low pass filters 418 and 419 are electrically coupled to a divider circuit 420.

The divider circuit 420 divides the difference signal with the summed signal, producing a normalized signal. The normalized signal represents the position of the sweep on the position sensitive detector, without regard for the intensity variation across the sweep. In this manner, the height of the wafer 320 can be determined without errors caused by intensity variations of the reflective beam due to, inter alia, pattern features on the surface 40. The normalized signal may be applied depending upon the application. In one embodiment, the normalized signal is filtered by a third low pass filter 421 coupled between the divider circuit 420 and an open loop response circuit, such as a monitor 350, where a map of height variations can be observed. Alternatively, the normalized signal can be used on a closed loop system where it is once again filtered by a loop filter 422, and electrically coupled to piezo stage 349 via an amplifier 423.

The height correction system described was evaluated on a wide range of wafers both bare and patterned with FIG. 18 showing a typical result. Line 363 shows the APS output of the processing circuitry versus height position. The height position was measured by a mechanical gauge. Over a nearly 70 micron change in height, the output voltage of the system changed by one volt, with the slope of line 363 remaining linear.

FIG. 19 demonstrates the effectiveness of the piezostage in adjusting the surface height dynamically, to obtain an optimum height of the surface. A piezostage is a stage the height of which can be converted by a piezoelectric stack. Line 364 represents the variation in surface height along a 10 cm strip of the surface, without compensating for the variations. This is referred to as an open loop response. Over the 10 cm strip, the height of the surface varied by almost 4 microns. Line 365, on the other hand, represents the height variation along the same 10 cm strip, except, in this instance, the piezostage compensates for the height variations. It is clear that the stage was able to maintain the wafer at a constant height with less than 0.5 micron of variation, as shown by line 365.

The above-described invention is particularly useful in the strip-unit-to-strip-unit comparison of a patterned wafer, where it is important for a strip unit scanned to be registered with an adjacent strip unit scanned previously as discussed above. Further, locking the signals produced by the detector to the sweep frequency facilitates strip-unit-to-strip-unit comparison by allowing dynamic adjustment of the height and tilt of the surface on the fly as the wafer is scanned, in accord with measured variations in height and tilt of the surface.

Applicants have found that other measures, used together with the above described system for dynamic height correction, can achieve a pixel misregistration error of less than ±1 pixel. Such measures are outlined below.

An analysis was performed which determined the maximum possible errors which could be generated from four primary sources. The first source is the system mechanics. This includes the dynamic position tolerances of the XY stage of the type described above in directions both parallel and orthogonal to the scanning beam, and the vibration or relative motion of the optical system to the stage. (The solution was an airbearing stage with extremely tight tolerances, and a very rigid structure containing the optics and stage, supported on pneumatic isolators.) The second source is any Z height deviations of the type described above in the wafer under inspection. Z height deviations for a grazing angle illuminator directly translate into X errors in the registration of two adjacent strip units. Z height deviations are corrected using the height correction system described above. The third source arises from errors in the synchronization of the sweep generation and data acquisition to the X position of the stage. (The timing electronics board in the system decodes the X stage quadrature signals and synchronizes sweep generation and data acquisition to stage position.) The fourth source of error is beam scintillation due to airflow through the scanning optics. Air flow must be kept at a sufficiently low velocity to avoid deflection of the scanning beam. Specification and design of the subsystems were focused on minimizing these system errors.

As will be apparent to those skilled in the art, the system registration requirements could be met by buffering any two strip units in a sufficiently large memory buffer, registering the images electronically, and then applying the detection and verification processes described above. This method could be employed by this invention.

System Features

When used together, various combinations of the above described inventive features can be used to achieve superior inspection sensitivity with adequate throughput for in-line inspection and at reasonable cost. Before these combinations are explored, it is useful to explain in some detail sensitivity and throughput issues related to the illumination optics of the system in reference to FIGS. 1A–6. FIGS. 1A–6, the accompanying description of these figures set forth above, and the following description on improved sensitivity of detection and throughput considerations are taken from parent application "Scanning System for Inspecting Anomalies on Surfaces," by Mehrdad Nikoonahad and Stanley E. Stokowski, Ser. No. 08/499,995 filed Jul. 10, 1995.

Improved Detection Sensitivity

As known to those skilled in the art, when AOD 30 is used to cause beam 38 to scan along each short sweep such as 50, time will be required at the beginning of the scan for the sound waves generated by the transducer portion of the AOD to fill the optical aperture so as to begin deflecting the beam. Preferably, no data samples are taken at the beginning part of the scan during this time. If L is the total length of the scan of the beam, and l the length of the portion of L from which data samples are taken, the ratio of l to L is a quantity called the duty factor η, given by l=ηL. This duty factor is a measure of the amount of overhead on the system due to this property of the AOD. The quantity 1 is thus the length of the sweep referred to above.

From the point of view of sensitivity of detection, it is desirable to design the illumination optics portion of system 20 so that the minimum width w of the illuminated spot 10 is minimized. The minimum width w is proportional to the focal length of lens 36 and inversely proportional to the beam diameter of beam 28 and 32. Therefore, the minimum width w can be reduced by reducing the focal length of lens 36 or increasing diameter of beam 28, or both. If the focal length of lens 36 is increased, this will increase the length of sweep 50 which may be undesirable. If the diameter of beam 28 becomes comparable to the clear aperture of the crystal in AOD 30, this will produce higher level sidelobes which is undesirable. As noted above, an increased level of sidelobes will increase the background signal level. Applicants discovered that it is preferable for the ratio between the clear aperture of the crystal in the AOD 30 and the diameter of beam 28 and 32 to exceed 1.2. This ratio is denoted k.

It is possible to increase the beam diameter of beam 28 and 32 by employing a large AOD crystal, while maintaining k to be above 1.2. However, in addition to cost considerations, a larger AOD crystal will cause larger losses, thereby degrading the diffraction efficiency of the AOD device. For this reason, it is desirable to employ AOD crystals that are as small as possible, while at the same time meeting the sensitivity and throughput requirements. Assuming that the beam 28 that is entering the AOD 30 has a Gaussian intensity profile, the clear aperture of the AOD, D, satisfies:

$$D = 4kLv/\pi w \Delta f, \qquad (3)$$

where L is the total scan length, v is the acoustic velocity in the AOD crystal 30, w is the length of the short axis of the elliptical spot (or the minimum width of the spot if not elliptical) on surface 40, $\Delta f$ or (f2–f1) is the bandwidth of the AOD 30, T is the duration of a sweep, and $\pi$ is the ratio of the circumference of a circle to its diameter, commonly known as "pi" The constant k is preferably in the range 1.2–5. In one embodiment, k is 1.7 and L is in the range of about 2–10 millimeters.

Throughput Considerations

For a semiconductor wafer inspection instrument to be used for in-line inspection for inspecting the entire surfaces of wafers, throughput considerations are paramount. Therefore, in addition to the sensitivity capability described above, it is also desirable for the wafer inspection system of this invention to have a high throughput. Throughput, in this context, refers to the number of semiconductor wafers inspected per hour. The time required for inspecting semiconductor wafers first includes the time required for the illuminating light beam to scan the entire surface of the wafer. To perform the above-described short sweep, the time required to scan the entire surface depends on a number of factors. One factor obviously is the angle of illumination of the illuminating beam, or the value of $\Theta$, that is the angle between the illuminating beam and normal 150 to surface 40 to be inspected shown in FIG. 3. The larger the value of $\Theta$ (that is, the smaller the grazing angle of incidence), the more elongated would be the shape of the spot 10 in FIG. 1A, and the larger is the area being inspected. Another factor affecting throughput is the fact that the intensity distribution of the illuminating beam is typically not flat but varies, such as in the form of a Gaussian distribution. Therefore, the intensity of scattering from a location on a surface would depend on the intensity of the illuminating light at that location. In order to compensate for such variation of intensity, a number of data points are obtained from the scattering from the particular location of the surface as the spot is moved across the location in a manner illustrated in FIG. 5 described above.

As described above, the minimum width (that is, length of short axis) of the spots 10, 10', 10" is w. If the angle between the illuminating light beam and normal 150 to the surface 40 to be inspected is $\Theta$ as shown in FIG. 3, then the magnitude of the long axis of the ellipse 10, 10', 10" is w/cos$\Theta$. Therefore, in each short sweep, the area illuminated sequentially by the illuminating light beam is given by (w/cos$\Theta$)*l, where l is the length of the sweep such as 50. Thus if the radius of surface 40 is R and T is the time it takes for the beam to scan the short sweep, then the time it takes for the illuminating beam to scan across the entire wafer is given by N$\pi$R$^2$Tcos$\Theta$/lw (where the time required for illumination optics to move the beam between strips, such as strips 54, 56 has not been accounted for). In this expression, N is the number of pixels along the X axis in each spot such as 10, 10', 10", since each pixel on the surface will be illuminated N number of times during the scanning process to account for the variation of intensity of illumination in the X direction as described above. In the preferred embodiment illustrated in FIG. 5, where four data points are taken in both the X and Y directions, N has the value 4.

In the scanning process described above in reference to FIGS. 2–4, it is noted that it will require time for the illumination optics to move the illumination spot between strips, such as strips 54 and 56. If $\tau$ is the time required to move the illumination spot between strips, then this additional time should be accounted for to give the total time required to scan the entire wafer surface. In the preferred embodiment described above, XY stage 124 which includes a motor is used in order to move the surface so as to move the illumination spot from the position for scanning one strip on the surface to the adjacent strip as shown in FIGS. 2 and 3. For a circular wafer of radius R, the spot will need to be moved 2 R/rL times between adjacent strips to move the spot across all the strips on the entire wafer, so that the additional time required is 2 R$\tau$/$\eta$L, where $\eta$ is the duty factor, given by equation 4 below:

$$\eta = 1 - \frac{4kL}{\Pi wT\Delta f} \quad (4)$$

Therefore, the total time $t_s$ it takes to scan the entire surface of a wafer with radius R is given by equation 5 below:

$$t_s = \frac{N\Pi R^2 T \cos\theta + 2R\tau w}{\eta L w} \quad (5)$$

where the definitions of equations (4), (5) are given above in relation to equation (3).

From equation (5) above, it is evident that the shorter the time T to scan along a sweep such as 50, the shorter will be the time required to scan the entire wafer and therefore the higher the throughput. The time T is referred to as the chirp duration which also determines the data rate.

From equation (3) above, for a given spot size, length of the sweep and the value of k, it is evident that the larger the bandwidth $\Delta$f or f2–f1, the smaller will be the clear aperture required of the AOD. To get maximum bandwidth from the AOD, the AOD should be operated at the highest possible frequency and one then expects to get one octave bandwidth around the center frequency of the transducer. However, the acoustic losses in the AOD crystal increase with the center frequency of operation. Large acoustic losses can cause two major problems: reduction in diffraction efficiency and thermal errors induced in the crystal. A reduction in the diffraction efficiency reduces the sensitivity of the system to small particles. When the AOD transducer is operated at high frequencies, more of the acoustic energy will be converted into heat which sets up thermal gradients in the AOD crystal. Such thermal gradients would cause errors by degrading the focal spot which in turn leads to a reduction in sensitivity for detecting anomalies. It is therefore advantageous to minimize the acoustic losses by selecting as low a center frequency of the transducer as possible. A compromise should then be found to yield acceptable detection sensitivity as well as acceptable throughput. Applicants found that a center frequency in the range of 50–300 megahertz and a bandwidth preferably within the range of 50–250 megahertz would be acceptable. The AOD 30 is preferably driven by a linear frequency modulated (FM) chirp signal from generator 80 in FIG. 2. The quantity $\pi$L or l is the effective length of the sweep; in the preferred embodiment the effective length l is in the range of 2 to 10 mm but more preferably has a value of about 5.47 mm, where L has the value of 6.2 mm.

From equation (5) above, it is seen that the larger the angle $\Theta$, the higher will be the throughput, since the illuminated spot will cover a larger area of the surface. But as noted above, the larger the spot size, the lower will be the sensitivity of detection. In the preferred embodiment, $\Theta$ is in the range of 10°–85° and more preferably in the range of 50°–80°.

Also from equation 5 above, it is evident that the larger the number of samples taken across the illuminated spot diameter, the more time it would take to scan the wafer. In the preferred embodiment, the number of samples taken across the illuminated spot diameter along both orthogonal axes (X, Y) is in the range of 2–10.

For sensitivity considerations, it is preferable for the minimum width w of the illuminated area to be in the range of 5–15 microns. If $\Theta$ is in the range of 50°–80°, then the illuminating beam will illuminate the sweeps such as 50 at such speed that the surface is inspected at a speed not less than about 2.5cm$^2$/s, and more preferably in a range of about 2.53–3.8cm$^2$/s.

From equation (5) above, if the time required for moving the wafer or the illumination beam so that the illuminated spot is transferred between adjacent strips such as strips 54, 56 is taken into account, then the average speed for scanning the entire surface 40 will be reduced compared to that for scanning a sweep such as sweep 50. Furthermore, the speed for inspecting the entire wafer is further reduced because each pixel on the wafer is scanned multiple times as described above in reference to FIG. 6. If the value of $\tau$ is about 0.3 seconds, and where the scan speed along each sweep is not less than 2.5cm$^2$/s, then the average speed for the illumination beam scanning the entire surface is not less than about 1.5cm$^2$/s. In the preferred embodiment, the average speed is preferably within the range of about 1.5–5cm$^2$/s. If the surface 40 scanned has dimensions of not less than 200 millimeters in any direction along the surface, then the illumination beam will scan the entire surface in about 50–90 seconds. As noted above, the length of the sweeps such as sweep 50 is preferably small compared to the dimensions of the surface 40 inspected. In the preferred embodiment, these sweeps are substantially in the range of about 2–10 millimeters.

In the preferred embodiment, generator 80 supplies a linear FM chirp signal to drive the AOD so that the chirp duration is preferably in the range of 20–200 microseconds, and more preferably in the range of about 80–120 microseconds. The beam 28 before deflection by the AOD 30 has at least one cross-sectional dimension (e.g. the longer dimension) in the range of about 4–12 millimeters. Preferably, the scan lens 36 is placed substantially at one focal length away from AOD 30 so that beam 38 scans the surface 40 telecentrically.

From the above, it will be evident that the objective of the invention of the high sensitivity and high throughput surface inspection system has been achieved using moderate data rate (e.g. 20 Mhz) at modest cost for the data sampling and processing electronics can still be achieved. This system is capable of inspecting patterned wafers with 0.25 and 0.35 micron design rules, such as patterned wafers for 64 and 256 megabit DRAM technology. The system is capable of detecting contaminant particles and pattern defects on memory and logic devices. With the present state-of-the-art robotic implementation for removing and replacing wafer 40 on stage 124 ready for system 20 to inspect and the inherent delay (about 25 seconds/wafer) involved therein, system 20 described above is capable of inspecting in excess of about 40 wafers per hour for 150 millimeter diameter wafers (6-inch wafers), in excess of about 20 wafers per hour for 200 millimeter diameter wafers (8-inch wafers) and in excess of about 10 wafers per hour for 300 millimeter diameter wafers (12-inch wafers).

While in the invention described above, the sweeps are described and illustrated as straight lines, it will be understood that it is also possible for curved sweeps to be employed, such as where the wafer is rotated about an axis instead of translated along straight lines in the X and Y directions as described above. While in the preferred embodiment described above, the sweeps form arrays, each array covering a substantially rectangular strip of the wafer, it will be understood that other different arrangements of the sweeps are possible for covering the entire or substantially the entire surface 40; such and other variations are within the scope of the invention. As the spot 10 approaches the edge of surface 40, the length of the sweep may be reduced so that the spot does not fall outside surface 40. All the advantages described are obtained even though the sweeps are of different lengths if each of at least some of the sweeps has a span shorter than the dimensions of the surface.

Data Rate, Throughput, Sensitivity and Buffer Size

As described above, the data rate of the data processing subsystem is synchronized with the timing electronics 84 of FIG. 2 and therefore the scanning speed of the illumination system. The above-described inspection system enables data processing to be performed at a data rate of below 50 MHz (more preferably below 30 MHz at the state of the art of today, such as at 20 MHz) while still maintaining the above-described throughput. As discussed above, the throughput of the system is indicated by scanning speed in the sweep across each sweep, the scan speed covering each strip such as strips 54, 56, as well as the scan speed across a single wafer. Preferably sensitivity of the system is improved by the use of smaller spot size, such as one in the range of 5 to 15 micrometers. Uniformity of illumination is maintained since the sweeps are short—no more than about 2 to 10 mm in length.

Regarding the sampling frequency $f_s$ and average data rate $f_{av}$, a smaller spot diameter w and/or a shorter sweep time will increase the sampling frequency and average data rate. If one scans an effective length l during time T with a spot size w and takes N samples within w, the sampling frequency $f_s$, and average data rate $f_{av}$ for acquiring the data are given by:

$$f_s = NL/wT \qquad (6)$$

$$f_{av} = Nl/wT \qquad (7)$$

where as before, l is the effective length of the sweep and L is the total length of scan.

Although the data processing algorithm is generic and may be applied to imaging systems as described above, the specific circuit for data processing becomes system dependent. In the context of a laser scanning system that is the preferred embodiment, the size of the buffer for storing data from strip units is a direct function of the angle of illumination Θ, spot diameter w, effective scan length l and the width d of the strip unit, as well as the number N of samples taken from the point spread function in both X and Y directions. The number of samples along a sweep is given by Nl/w or NLη/w. In the X direction, the number of sweeps is given by: N d cos Θ/w, where d is the width of the strip in the X direction. It is, therefore, clear that for a fundamental repeating pattern, d shown in FIG. 12, the minimum required strip unit buffer size is given by:

Minimum required buffer size in bytes=$2N^2 l \cos \Theta/w^2$

Where it has been assumed that each sample occupies two bytes of memory.

While the invention has been described by reference to preferred embodiments, it will be understood that modifications and changes can be made without departing from the scope of the invention which is to be defined only by the appended claims.

What is claimed is:

1. An inspection system for detecting anomalies on a surface, comprising:

means for optically scanning the surface;

means for collecting light scattered by the surface and deriving an intensity value for at least a first pixel location from the collected light;

means for determining an error threshold for said at least first pixel location from intensity values stored for at least a corresponding second pixel location and its neighboring pixel locations of a reference image of the surface, said error threshold being determined by the difference between an intensity value stored for the second pixel location and a maximum or minimum of intensity values stored for the second pixel location and its neighboring pixel locations in the reference image; and means for identifying anomalies by comparing the difference between the intensity value for the at least first pixel location and that stored for the second pixel location to said error threshold.

2. The system of claim 1, said surface having a plurality of repeating patterns thereon, said at least first and second pixel locations being in adjacent patterns, wherein said determining means includes buffer means storing the intensity values for said second pixel location and its neighboring pixel locations of the reference image of the surface.

3. The inspection system of claim 1, wherein the intensity value of collected light for the first pixel location and the stored intensity values for said second pixel location are spatially registered to an accuracy of better than plus or minus a pixel location.

4. The system of claim 3, wherein said optically scanning means directs a focused light beam at an oblique angle to scan said surface, said system further comprising means for measuring specular reflection of the light beam and for dynamically correcting the height of the surface during the scan.

5. The system of claim 1, wherein the intensity value of collected light for the first pixel location and the stored intensity values for said second pixel location are spatially registered to an accuracy of better than plus or minus a multiple of a pixel location, and wherein said determining means interpolates by multiplying the error threshold by a multiple.

6. The system of claim 1, said collecting and deriving means deriving said intensity value for said first pixel location from the collected light at said first pixel location and its adjacent pixel locations.

7. The system of claim 1, said system having a point spread function with said second pixel location at or near the peak of the function, wherein the neighboring pixel locations adjacent to said second pixel location form a two dimensional array defining a matrix having a center with said second pixel location at the center of the matrix, said matrix covering substantially the point spread function of the system above a predetermined intensity level.

8. The system of claim 7, said matrix being a three by three matrix.

9. The system of claim 1, wherein said identifying means also compares the difference between the intensity value for the first pixel location and that stored for the second pixel location to a second threshold that is proportional to the intensity value stored for the second pixel location.

10. The system of claim 1, wherein said identifying means also compares the difference between the intensity value for the first pixel location and that stored for the second pixel location to a third threshold that is a function of system noise.

11. The system of claim 1, wherein said collecting and deriving means derives intensity values for said first pixel location and for its adjacent pixel locations from the collected light; said system further comprising:
  a memory storing intensity values for the second pixel location of a reference image of the surface, and for neighboring pixel locations of the second pixel in the reference image corresponding in position to the adjacent pixel locations of the at least first pixel location;
  wherein said identifying means also identifies anomalies by ascertaining whether each of some of the intensity values for the first pixel location and its adjacent pixel locations exceeds or is less than that stored for the corresponding pixel location of the second pixel location and its neighboring pixel locations.

12. The system of claim 11, said system having a point spread function with said first pixel location at or near the peak of the function, wherein the pixel locations adjacent to said first pixel location form a two dimensional first matrix with the at least first pixel location at the center of the first matrix, said first matrix covering substantially the point spread function of the system above a predetermined threshold, said neighboring pixel locations of the second pixel location forming a second matrix of the same size as the first matrix with the second pixel location at the center of the second matrix.

13. The system of claim 12, wherein said identifying means identifies anomalies by ascertaining whether each of the intensity values for the first pixel location and its adjacent pixel locations exceeds or is less than that stored for the corresponding pixel location of the second pixel location and its neighboring pixel locations.

14. The system of claim 12, said first and second matrices being three by three matrices.

15. The system of claim 1, further comprising means for verifying the identified anomaly by ascertaining whether the intensity value of the first pixel location is a multiple of the intensity value of second pixel location, said multiple being in the range of 2 to 16.

16. The system of claim 1, further comprising:
  a memory storing intensity values for said second pixel location and its neighboring pixel locations; and
  means for verifying an identified anomaly by convolving a convolution matrix with the intensity values at said first pixel location and its adjacent pixel locations to obtain a first convolved value, and with the intensity values at said second pixel location and its neighboring pixel locations to obtain a second convolved value, and determining whether the difference between the first and second convolved values exceeds a predetermined convolution threshold.

17. The system of claim 16, said convolution threshold being a function of system noise.

18. The system of claim 16, said convolution threshold being proportional to the second convolved value.

19. The system of claim 16, said system having a point spread function with said first pixel location at or near the peak of the function, wherein the pixel locations adjacent to said first pixel location form a two dimensional first pixel location matrix with the at least first pixel location at the center of the first pixel location matrix, said first pixel location matrix covering substantially the point spread function of the system, said neighboring pixel locations of the second pixel location forming a second pixel location matrix of the same size as the first pixel location matrix with the second pixel location at the center of the second pixel location matrix;
  wherein the verifying means convolves said convolution matrix with the intensity values at said first pixel location matrix to obtain said first convolved value and convolves said convolution matrix with the intensity values at said second pixel location matrix to obtain said second convolved value.

20. The system of claim 19, said convolution matrix and said first and second pixel location matrices being five by five matrices.

21. An inspection system for detecting anomalies on a surface, comprising:
  means for optically scanning the surface;
  means for collecting light scattered by the surface and deriving intensity values for said first pixel location and for its adjacent pixel locations from the collected light;
  a memory storing intensity values for a second pixel location of a reference image of the surface, said second pixel location corresponding in position to the at least first pixel location, and for neighboring pixel locations of the second pixel in the reference image corresponding in position to the adjacent pixel locations of the at least first pixel location;
  means for identifying anomalies by ascertaining whether each of some of the intensity values for the first pixel location and its adjacent pixel locations exceeds or is less than that stored for the corresponding pixel location of the second pixel location and its neighboring pixel locations.

22. The system of claim 21, said system having a point spread function with said first pixel location at or near the peak of the function, wherein the pixel locations adjacent to said first pixel location form a two dimensional first matrix with the at least first pixel location at the center of the first matrix, said first matrix covering substantially the point spread function of the system above a predetermined intensity level, said neighboring pixel locations of the second pixel location forming a second matrix of the same size as the first matrix with the second pixel location at the center of the second matrix.

23. The system of claim 22, said first and second matrices being three by three matrices.

24. The system of claim 21, said surface having a plurality of repeating patterns thereon, said at least first and second pixel locations being in adjacent patterns, wherein said determining means includes buffer means storing the intensity values for said second pixel location and its neighboring pixel locations of the reference image of the surface.

25. The inspection system of claim 21, wherein the intensity value of collected light for the first pixel location and the stored intensity values for said second pixel location are spatially registered to an accuracy of plus or minus a pixel location or better.

26. The system of claim 25, wherein said optically scanning means directs a focused light beam at an oblique angle to scan said surface, said system further comprising means for measuring specular reflection of the light beam and for dynamically correcting the height of the surface during the scan.

27. An inspection system for determining an anomaly on a surface, comprising:
   means for providing the intensity value for at least a first pixel location on the surface;
   a memory storing an intensity value for at least a second pixel location of a reference image of the surface, said second pixel location corresponding in position to the at least first pixel location;
   means for verifying the anomaly by ascertaining whether the intensity value of the at least first pixel location is a multiple of the intensity value of second pixel location, said multiple being in the range of 2 to 16.

28. The system of claim 27, said system having a point spread function with said at least first pixel location at or near the peak of the function, wherein the pixel locations adjacent to said first pixel location form a two dimensional first matrix with the at least first pixel location at the center of the first matrix, said first matrix covering substantially the point spread function of the system above a predetermined intensity level, said neighboring pixel locations of the second pixel location forming a second matrix of the same size as the first matrix with the second pixel location at the center of the second matrix;
   wherein said providing means provides said intensity value for said first pixel location by deriving an average intensity value from the intensity values at the first matrix; and
   wherein the intensity value for the second pixel location stored in said memory is an average of the intensity values at the second matrix.

29. The system of claim 28, said first and second matrices being three by three matrices.

30. An inspection system for determining an anomaly on a surface, comprising:
   means for providing the intensity values for at least a first pixel location and its adjacent pixel locations on the surface;
   a memory storing intensity values for a second pixel location of a reference image of the surface, said second pixel location corresponding in position to the at least first pixel location, and for neighboring pixel locations of the second pixel in the reference image corresponding in position to the adjacent pixel locations of the at least first pixel location;
   means for determining an anomaly by convolving a convolution matrix with the intensity values at said first pixel location and its adjacent pixel locations to obtain a first convolved value, and with the intensity values at said second pixel location and its neighboring pixel locations to obtain a second convolved value, and determining whether the difference between the first and second convolved values exceeds a predetermined convolution threshold.

31. The system of claim 30, said system having a point spread function with said first pixel location at or near the peak of the function, wherein the pixel locations adjacent to said first pixel location form a two dimensional first pixel location matrix with the at least first pixel location at the center of the first pixel location matrix, said first pixel location matrix covering substantially the point spread function of the system above a predetermined threshold, said neighboring pixel locations of the second pixel location forming a second pixel location matrix of the same size as the first pixel location matrix with the second pixel location at the center of the second pixel location matrix;
   wherein the verifying means convolves said convolution matrix with the intensity values at said first pixel location matrix to obtain said first convolved value and convolves said convolution matrix with the intensity values at said second pixel location matrix to obtain said second convolved value.

32. The system of claim 31, said convolution matrix and said first and second pixel location matrices being five by five matrices.

33. The system of claim 31, wherein said surface is that of a non-patterned surface.

34. The system of claim 31, said surface having a plurality of repeating patterns thereon, said at least first and second pixel locations being in adjacent patterns, wherein said determining means includes buffer means storing the intensity values for said second pixel location and its neighboring pixel locations of the reference image of the surface.

35. The system of claim 31, wherein the convolution matrix has a perimeter and a core, and wherein the values at the perimeter are positive and the values at the core are negative or the values at the perimeter are negative and the values at the core are positive.

36. The system of claim 35, wherein said values at the perimeter are equal, and said values at the core are also equal.

37. The system of claim 35, wherein the sum of said values at the perimeter and said values at the core is substantially zero.

38. The system of claim 30, said convolution threshold being a function of system noise.

39. The system of claim 30, said convolution threshold being proportional to the second convolved value.

40. An inspection method for detecting anomalies on a surface, comprising the steps of:
   optically scanning the surface;
   collecting light scattered by the surface and deriving an intensity value for at least a first pixel location from the collected light;
   determining an error threshold for said at least first pixel location from intensity values stored for at least a corresponding second pixel location and its neighboring pixel locations of a reference image of the surface, said error threshold being determined by the difference between the intensity value stored for the second pixel location and a maximum or minimum of intensity values stored for the second pixel location and its neighboring pixel locations in the reference image; and
   identifying anomalies by comparing the difference between the intensity value for the at least first pixel location and that stored for the second pixel location to said error threshold.

41. The method of claim 40, said surface having a plurality of repeating patterns thereon, said at least first and second pixel locations being in adjacent patterns, wherein said determining step includes storing the intensity values for said second pixel location and its neighboring pixel locations of the reference image of the surface.

42. The inspection method of claim 40, wherein said scanning, collecting and deriving steps are such that the intensity value of collected light for the first pixel location and the stored intensity values for said second pixel location are spatially registered to an accuracy of better than plus or minus a pixel location.

43. The method of claim 42, wherein said optically scanning step directs a focused light beam at an oblique angle to scan said surface, said method further comprising step of measuring specular reflection of the light beam and dynamically correcting the height of the surface during the scan.

44. The method of claim 40, wherein the intensity value of collected light for the first pixel location and the stored intensity values for said second pixel location are spatially registered to an accuracy of better than plus or minus a multiple of a pixel location, and
wherein said determining step interpolates by multiplying the error threshold by a multiple.

45. The method of claim 40, said collecting and deriving step deriving said intensity value for said first pixel location from the collected light at said first pixel location and its adjacent pixel locations.

46. The method of claim 40, said method characterized by a point spread function with said second pixel location at or near the peak of the function, wherein the pixel locations adjacent to said second pixel location form a two dimensional matrix having a center with said second pixel location at the center of the matrix, said matrix covering substantially the point spread function characterizing the method above a predetermined intensity level.

47. The method of claim 46, said matrix being a three by three matrix.

48. The method of claim 40, wherein said identifying step also compares the difference between the intensity value for the first pixel location and that stored for the second pixel location to a second threshold that is proportional to the intensity value stored for the second pixel location.

49. The method of claim 40, wherein said identifying step also compares the difference between the intensity value for the first pixel location and that stored for the second pixel location to a third threshold that is a function of noise inherent in the method.

50. The method of claim 40, wherein said collecting and deriving step derives intensity values for said first pixel location and for its adjacent pixel locations from the collected light; said method further comprising:
storing intensity values for the second pixel location of a reference image of the surface, and for neighboring pixel locations of the second pixel in the reference image corresponding in position to the adjacent pixel locations of the at least first pixel location;
wherein said identifying step also identifies anomalies by ascertaining whether each of some of the intensity values for the first pixel location and its adjacent pixel locations exceeds or is less than that stored for the corresponding pixel location of the second pixel location and its neighboring pixel locations.

51. The method of claim 50, said method characterized by a point spread function with said first pixel location at or near the peak of the function, wherein the pixel locations adjacent to said first pixel location form a two dimensional first matrix with the at least first pixel location at the center of the first matrix, said first matrix covering substantially the point spread function characterizing the method above a predetermined threshold, said neighboring pixel locations of the second pixel location forming a second matrix of the same size as the first matrix with the second pixel location at the center of the second matrix.

52. The method of claim 51, wherein said identifying step identifies anomalies by ascertaining whether each of the intensity values for the first pixel location and its adjacent pixel locations exceeds or is less than that stored for the corresponding pixel location of the second pixel location and its neighboring pixel locations.

53. The method of claim 51, said first and second matrices being three by three matrices.

54. The method of claim 40, further comprising step for verifying the identified anomaly by ascertaining whether the intensity value of the first pixel location is a multiple of the intensity value of second pixel location, said multiple being in the range of 2 to 16.

55. The method of claim 40, further comprising:
storing intensity values for said second pixel location and its neighboring pixel locations; and
verifying an identified anomaly by convolving a convolution matrix with the intensity values at said first pixel location and its adjacent pixel locations to obtain a first convolved value, and with the intensity values at said second pixel location and its neighboring pixel locations to obtain a second convolved value, and ascertaining whether the difference between the first and second convolved values exceeds a predetermined convolution threshold.

56. The method of claim 55, said convolution threshold being a function of noise inherent in the method.

57. The method of claim 55, said convolution threshold being proportional to the second convolved value.

58. The method of claim 55, said method characterized by a point spread function with said first pixel location at or near the peak of the function, wherein the pixel locations adjacent to said first pixel location form a two dimensional first pixel location matrix with the at least first pixel location at the center of the first pixel location matrix, said first pixel location matrix covering substantially the point spread function characterizing the method, said neighboring pixel locations of the second pixel location forming a second pixel location matrix of the same size as the first pixel location matrix with the second pixel location at the center of the second pixel location matrix;
wherein the verifying step convolves said convolution matrix with the intensity values at said first pixel location matrix to obtain said first convolved value and convolves said convolution matrix with the intensity values at said second pixel location matrix to obtain said second convolved value.

59. The method of claim 58, said convolution matrix and said first and second pixel location matrices being five by five matrices.

60. An inspection method for detecting anomalies on a surface, comprising the steps of:
optically scanning the surface;
collecting light scattered by the surface and deriving intensity values for said first pixel location and for its adjacent pixel locations from the collected light;
storing intensity values for a second pixel location of a reference image of the surface, said second pixel location corresponding in position to the at least first pixel location, and for neighboring pixel locations of the second pixel in the reference image corresponding in position to the adjacent pixel locations of the at least first pixel location;

identifying anomalies by ascertaining whether each of some of the intensity values for the first pixel location and its adjacent pixel locations exceeds or is less than that stored for the corresponding pixel location of the second pixel location and its neighboring pixel locations.

61. The method of claim 60, said method characterized by a point spread function with said first pixel location at or near the peak of the function, wherein the pixel locations adjacent to said first pixel location form a two dimensional first matrix with the at least first pixel location at the center of the first matrix, said first matrix covering substantially the point spread function characterizing the method above a predetermined intensity level, said neighboring pixel locations of the second pixel location forming a second matrix of the same size as the first matrix with the second pixel location at the center of the second matrix.

62. The method of claim 61, said first and second matrices being three by three matrices.

63. The method of claim 60, said surface having a plurality of repeating patterns thereon, said at least first and second pixel locations being in adjacent patterns, wherein said determining step includes storing the intensity values for said second pixel location and its neighboring pixel locations of the reference image of the surface.

64. The inspection method of claim 60, wherein the intensity value of collected light for the first pixel location and the stored intensity values for said second pixel location are spatially registered to an accuracy of plus or minus a pixel location or better.

65. The method of claim 64, wherein said optically scanning step directs a focused light beam at an oblique angle to scan said surface, said method further comprising step for measuring specular reflection of the light beam and for dynamically correcting the height of the surface during the scan.

66. An inspection method for determining an anomaly on a surface, comprising the steps of:

providing the intensity value for at least a first pixel location on the surface;

storing an intensity value for at least a second pixel location of a reference image of the surface, said second pixel location corresponding in position to the at least first pixel location;

verifying the anomaly by ascertaining whether the intensity value of the at least first pixel location is a multiple of the intensity value of second pixel location, said multiple being in the range of 2 to 16.

67. The method of claim 66, said method characterized by a point spread function with said at least first pixel location at or near the peak of the function, wherein the pixel locations adjacent to said first pixel location form a two dimensional first matrix with the at least first pixel location at the center of the first matrix, said first matrix covering substantially the point spread function characterizing the method above a predetermined intensity level, said neighboring pixel locations of the second pixel location forming a second matrix of the same size as the first matrix with the second pixel location at the center of the second matrix;

wherein said providing step provides said intensity value for said first pixel location by deriving an average intensity value from the intensity values at the first matrix; and wherein the intensity value for the second pixel location stored in said memory is an average of the intensity values at the second matrix.

68. The method of claim 67, said first and second matrices being three by three matrices.

69. An inspection method for determining an anomaly on a surface, comprising the steps of:

providing the intensity values for at least a first pixel location and its adjacent pixel locations on the surface;

storing intensity values for a second pixel location of a reference image of the surface, said second pixel location corresponding in position to the at least first pixel location, and for neighboring pixel locations of the second pixel in the reference image corresponding in position to the adjacent pixel locations of the at least first pixel location;

determining an anomaly by convolving a convolution matrix with the intensity values at said first pixel location and its adjacent pixel locations to obtain a first convolved value, and with the intensity values at said second pixel location and its neighboring pixel locations to obtain a second convolved value, and determining whether the difference between the first and second convolved values exceeds a predetermined convolution threshold.

70. The method of claim 69, said method characterized by a point spread function with said first pixel location at or near the peak of the function, wherein the pixel locations adjacent to said first pixel location form a two dimensional first pixel location matrix with the at least first pixel location at the center of the first pixel location matrix, said first pixel location matrix covering substantially the point spread function characterizing the method above a predetermined threshold, said neighboring pixel locations of the second pixel location forming a second pixel location matrix of the same size as the first pixel location matrix with the second pixel location at the center of the second pixel location matrix;

wherein the verifying step convolves said convolution matrix with the intensity values at said first pixel location matrix to obtain said first convolved value and convolves said convolution matrix with the intensity values at said second pixel location matrix to obtain said second convolved value.

71. The method of claim 70, said convolution matrix and said first and second pixel location matrices being five by five matrices.

72. The method of claim 70, wherein said surface is that of a non-patterned surface.

73. The method of claim 70, said surface having a plurality of repeating patterns thereon, said at least first and second pixel locations being in adjacent patterns, wherein said determining step includes storing the intensity values for said second pixel location and its neighboring pixel locations of the reference image of the surface.

74. The method of claim 70, wherein the convolution matrix has a perimeter and a core, and wherein the values at the perimeter are positive and the values at the core are negative or the values at the perimeter are negative and the values at the core are positive.

75. The method of claim 74, wherein said values at the perimeter are equal, and said values at the core are also equal.

76. The method of claim 74, wherein the sum of said values at the perimeter and said values at the core is substantially zero.

77. The method of claim 69, said convolution threshold being a function of noise inherent in the method.

78. The method of claim 69, said convolution threshold being proportional to the second convolved value.

79. A system for detecting anomalies on a surface; comprising:
- means for directing a focused beam of light at a grazing angle toward said surface;
- means for causing relative motion between the beam and the surface so that the entire surface is scanned with said beam;
- means for detecting the specular reflection from the said surface and dynamically measuring the height of the said surface during scan;
- means for dynamically correcting the height of said surface during scan;
- means for collecting light scattered from the surface and converting such light into an electrical signal;
- means for digitally processing said electrical signal for detecting anomalies, said digital processing means detecting anomalies by comparing the difference between the intensity value for at least a first pixel location and that stored for at least a second pixel location of a reference image of the surface to an error threshold, said error threshold being determined by the digitally processing means from the difference between the intensity value stored for the second pixel location and a maximum or minimum of intensity values stored for the second pixel location and its neighboring pixel locations of the reference image.

80. The system of claim 79, said directing means directing said beam to illuminate an area on the surface defining a spot, wherein the size of the spot is in the range of 5 to 15 micrometers.

81. The system of claim 79, wherein the grazing angle of illumination of the beam is in the range of 10 to 85 degrees.

82. The system of claim 79, wherein said relative motion causing means causes relative motion between the beam and the surface so that the beam scans a scan path covering substantially the entire surface, said path including a plurality of strips of sweeps, wherein each of at least some of such sweeps has a span shorter than the dimensions of the surface.

83. The system of claim 82, wherein the span of at least some of such sweeps is in the range of 2 to 10 mm.

84. The system of claim 79, said directing means directing said beam to illuminate a plurality of areas on the surface during the scan, each area on the surface defining a spot, said collecting and converting means converting the collected light into electrical signals representing light collected from 2 to 10 pixels within each spot.

85. The system of claim 79, wherein the detecting and measuring means includes a position sensitive detector for detecting the specular reflection from the surface and measuring the surface height of the wafer.

86. The system of claim 85, said dynamically correcting means including a piezostage, wherein the position sensitive detector provides a DC voltage output for controlling the piezostage which can dynamically correct the height of the wafer in response to the DC voltage output.

87. The system of claim 86, said digitally processing means detecting anomalies by comparing the intensity value for at least a first pixel location and that stored for at least a second pixel location of a previously scanned reference image of the surface, wherein the dynamically correcting means corrects the height of the wafer so that the first and second pixel locations are spatially aligned to within 0.25 of a pixel location.

88. The system of claim 79, said surface having a repeating pattern thereon, wherein said collecting and converting means collects light scattered by the surface at or near a first pixel location in a first pattern of the repeating pattern and converts such light into a first signal, and said processing means including a buffer for storing the electrical signal for a second pixel location from a pattern adjacent to said first pattern for comparison with the first signal.

89. A method for detecting anomalies on a surface; comprising the steps of:
- directing a focused beam of light at a grazing angle toward said surface;
- causing relative motion between the beam and the surface so that the entire surface is scanned with said beam;
- detecting the specular reflection from the said surface and dynamically measuring the height of the said surface during scan;
- dynamically correcting the height of said surface during scan;
- collecting light scattered from the surface and converting such light into an electrical signal; and
- digitally processing said electrical signal for detecting anomalies, said digitally processing step detecting anomalies by comparing the difference between the intensity value for at least a first pixel location and that stored or at least second pixel location of a reference image of the surface to an error threshold, said error threshold being determined in the digitally processing step by the difference between the intensity value stored for the second pixel location and a maximum or minimum of intensity values stored for the second pixel location and its neighboring pixel locations of the reference image.

90. The method of claim 89, said directing step directing said beam to illuminate an area on the surface defining a spot, wherein the size of the spot is in the range of 5 to 15 micrometers.

91. The method of claim 89, wherein the grazing angle of illumination of the beam is in the range of 10 to 85 degrees.

92. The method of claim 91, wherein said relative motion causing step causes relative motion between the beam and the surface so that the beam scans a scan path covering substantially the entire surface, said path including a plurality of strips of sweeps, wherein each of at least some of such sweeps has a span shorter than the dimensions of the surface.

93. The method of claim 91, said directing step directing said beam to illuminate a plurality of areas on the surface during the scan, each area on the surface defining a spot, said collecting and converting step converting the collected light into electrical signals representing light collected from 2 to 10 pixels within each spot.

94. The method of claim 91, said digitally processing step detecting anomalies by comparing the intensity value for at least a first pixel location and that stored for at least a second pixel location of a previously scanned reference image of the surface, wherein the dynamically correcting step corrects the height of the wafer so that the first and second pixel locations are spatially aligned to within 0.25 of a pixel location.

95. A method for detecting anomalies on a surface of a semiconductor wafer; comprising:
- directing a focused beam of light towards said surface to illuminate an area of the surface defining a spot;
- causing relative motion between the beam and the wafer so that the beam scans a serpentine path covering substantially the entire surface;
- collecting light scattered along said path for detecting anomalies and converting the collected light to an electrical signal;

wherein the spot size and said directing and causing steps are such that the beam substantially inspects the entire surface of the wafer at a throughput in excess of about 40 wafers per hour for 150 mm diameter wafers, at a throughput in excess of about 20 wafers per hour for 200 mm diameter wafers, and at a throughput in excess of about 10 wafers per hour for 300 mm diameter wafers; and digitally processing said electrical signal for detecting anomalies at a data clock rate less than 50 MHz.

96. The method of claim 95, said directing step being such that the spot has a spot size whose minimum dimension is in the range of about 5 to 15 microns.

97. A method for detecting anomalies on a surface, comprising the steps of:

directing a focused beam of light towards said surface to illuminate an area of the surface defining a spot;

causing relative motion between the beam and the surface so that the beam scans a serpentine path covering substantially the entire surface;

collecting light scattered along said path for detecting anomalies and converting the collected light to an electrical signal;

wherein the spot size and said directing and causing steps are such that the surface is inspected at a speed not less than about 1.5 cm²/s; and digitally processing said electrical signal for detecting anomalies at a data clock rate of less than 50 MHz.

98. The method of claim 97, said directing step being such that the spot has a spot size whose minimum dimension is in the range of about 5 to 15 microns.

99. A method for detecting anomalies on a surface, comprising the steps of:

directing a beam of light towards said surface to illuminate an area of the surface defining a spot;

causing relative motion between the beam and the surface so that the beam scans a serpentine path covering substantially the entire surface; and collecting light scattered along said path for detecting anomalies and converting the collected light to an electrical signal;

said surface having dimensions of not less than 200 mm in any direction along the surface, wherein said directing and causing steps are such that the beam scans substantially the entire surface in about 50 to 90 seconds; and digitally processing said electrical signal for detecting anomalies at a data clock rate of less than 50 MHz.

100. The method of claim 96, wherein the span of at least some of such sweeps is in the range of 2 to 10 mm.

101. The method of claim 99, said directing step being such that the spot has a spot size whose minimum dimension is in the range of about 5 to 15 microns.

102. A method for detecting anomalies on a surface, comprising the steps of:

directing a focused beam of light towards said surface to illuminate an area of the surface defining a spot whose size is in the range of about 5 to 15 micrometers;

causing relative motion between the beam and the surface so that the beam scans a serpentine path covering substantially the entire surface, said surface having dimensions of not less than 200 mm in any direction along the surface, wherein said directing and causing steps are such that the beam scans substantially the entire surface in about 50 to 90 seconds;

collecting light scattered along said path for detecting anomalies and converting the collected light to an electrical signal; and digitally processing said electrical signal for detecting anomalies at a data clock rate of less than 50 MHz.

103. The method of claims 101, wherein the spot size and said directing and causing steps are such that the beam substantially inspects the entire surface of the wafer at a throughput in excess of about 40 wafers per hour for 150 mm diameter wafers, at a throughput in excess of about 20 wafers per hour for 200 mm diameter wafers, and at a throughput in excess of about 10 wafers per hour for 300 mm diameter wafers.

104. The method of claim 101, wherein said relative motion causing step causes relative motion between the beam and the surface so that the beam scans a scan path covering substantially the entire surface, said path including a plurality of strips of sweeps, wherein each of at least some of such sweeps has a span shorter than the dimensions of the surface.

105. The method of claim 103, said directing step directing said beam to illuminate a plurality of areas on the surface during the scan, each area on the surface defining a spot, said collecting and converting step converting the collected light into electrical signals representing light collected from N pixels within each spot, N being in the range of 2 to 10.

106. The method of claim 104, said data clock rate being proportional to N and the span of the sweeps and inversely proportional to the size of the spot.

107. A system for detecting anomalies on a surface, comprising:

means for directing a focused beam of light towards said surface at an oblique angle of θ from the normal direction to the surface to illuminate a plurality of areas on the surface during the scan, each such illuminated area on the surface defining a spot of size w, said collecting and converting step converting the collected light into electrical signals representing light collected from N pixels within each spot;

means for causing relative motion between the beam and the surface so that the beam scans a serpentine path covering substantially the entire surface, said path including a plurality of strips of sweeps of effective length l shorter than the dimensions of the surface, wherein the beam scans each sweep in time T;

means for collecting light scattered along said path for detecting anomalies and converting the collected light to an electrical signal; and means for digitally processing said electrical signal for detecting anomalies, at a data clock rate substantially proportional to Nl/wT.

108. The system of claim 106, said surface having a repeating pattern thereon, wherein said collecting and converting means collects light scattered by the surface at or near a first pixel location in a first pattern of the repeating pattern and converts such light into a first signal, and said processing means including a buffer for storing a second electrical signal for a second pixel location from a pattern adjacent to said first pattern for comparison with the first signal;

wherein the processing means includes a buffer for storing the second electrical signal, said buffer means having a size proportional to $N^2 ld \cos\theta/w^2$.

109. The system of claim 1, wherein each of the intensity values stored for the second pixel and for its neighboring pixel locations is an averaged intensity value over a neighborhood around each respective pixel location, and the intensity value for the first pixel location derived by the collecting and deriving means is an average of intensity values over a neighborhood around the first pixel location.

110. The system of claim 1, said determining means including a circuit for finding the maximum or minimum of stored intensity values for the second pixel location and its neighboring pixel locations in the reference image.

111. The method of claim 40, wherein each of the intensity values stored for the second pixel and for its neighboring pixel locations is an averaged intensity value over a neighborhood around each respective pixel location, and the intensity value for the first pixel location derived in the collecting and deriving step is an average of intensity values over a neighborhood around the first pixel location.

112. An inspection system for detecting anomalies on a surface, comprising:

means for optically scanning the surface;

means for collecting light scattered by the surface and deriving an intensity value for at least a first pixel location from the collected light;

means for determining an error threshold for said at least first pixel location from intensity values stored for at least a corresponding second pixel location and its neighboring pixel locations of a reference image of the surface, said error threshold being determined by the difference between two intensity values stored for the second pixel location and its neighboring pixel locations in the reference image; and means for identifying anomalies by comparing the difference between the intensity value for the at least first pixel location and that stored for the second pixel location to said error threshold.

113. An inspection method for detecting anomalies on a surface, comprising the steps of:

optically scanning the surface;

collecting light scattered by the surface and deriving an intensity value for at least a first pixel location from the collected light;

determining an error threshold for said at least first pixel location from intensity values stored for at least a corresponding second pixel location and its neighboring pixel locations of a reference image of the surface, said error threshold being determined by the difference between two intensity values stored for the second pixel location and its neighboring pixel locations in the reference image; and identifying anomalies by comparing the difference between the intensity value for the at least first pixel location and that stored for the second pixel location to said error threshold.

* * * * *